(12) United States Patent
Tuite et al.

(10) Patent No.: US 6,291,205 B1
(45) Date of Patent: Sep. 18, 2001

(54) METHOD OF INCREASING PRODUCTION OF DISULFIDE BONDED RECOMBINANT PROTEINS BY SACCHAROMYCES CEREVISIAE

(75) Inventors: Michael F. Tuite, Chartham Hatch; Robert B. Freedman, Canterbury, both of (GB); Loren D. Schultz, Harleysville, PA (US); Ronald W. Ellis, Newton, MA (US); Henry Z. Markus, Wyncote; Donna L. Montgomery, Chalfont, both of PA (US)

(73) Assignees: Merck & Co., Inc., Rahway, NJ (US); University of Kent at Canterbury, Kent (GB)

( * ) Notice: Subject to any disclaimer, the term of this patent is extended or adjusted under 35 U.S.C. 154(b) by 0 days.

(21) Appl. No.: 07/901,713

(22) Filed: Jun. 12, 1992

(51) Int. Cl.[7] ............... C12P 21/02; C12N 1/19
(52) U.S. Cl. ................ 435/69.1; 435/254.21
(58) Field of Search ............... 435/69.1, 69.2, 435/69.7, 69.8, 233, 256, 254.21

(56) References Cited

U.S. PATENT DOCUMENTS

| | | | |
|---|---|---|---|
| 5,578,466 | * 11/1996 | Hayano et al. | 435/69.7 |
| 5,700,678 | 12/1997 | Toyoshima et al. | 435/233 |
| 5,874,247 | 2/1999 | Toyoshima et al. | 435/69.1 |

FOREIGN PATENT DOCUMENTS

0293793 * 12/1988 (EP) .............. C12N/15/00

OTHER PUBLICATIONS

Freedman, Trends. Biochem. Sci., 9 pp. 438–441 (1984).
Roth & Pierce, Biochem., 26 pp. 4179–4182 (1987).
Bulleid & Freedman, Nature, 335 pp. 649–650 (1988).
Freedman, et al. Biochem. Soc. Symp., 55 pp. 167–192 (1989).
Scherens, B., et al. Yeast, 7 pp. 185–193, (1991).
Farquhar, R. et al., Gene, 108 pp. 81–89 (1991).
Creighton, et al., J. Mol. Biol., 142 pp. 43–62 (1980).
Freedman, et al. Biochem. Soc. Trans., 16 pp. 96–99 (1988).
Gilbert, Biochem., 28 pp. 7298–7305 (1989).
Lundstrom & Holmgren, J. Biol. Chem., 265 pp. 9114–9120 (1990).
Hawkins & Freedman, Biochem. J., 275 pp. 335–339 (1990).
Rothman, Cell, 59 pp. 591–601 (1989).
Hillson, et al. Methods Enzymol., 107 pp. 281–292 (1984).
Kaska et al., Biochem. J., 268 pp. 63–68 (1990).
Williams et al. FEBS Letters, 2 pp. 133–135 (1968).
Edman et al. Nature, 317 pp. 267–270 (1985).
Yamauchi et al. Biochem. Biophys. Res., Comm. 146 pp. 1485–1492 (1987).
Pihalajaniemi et al. EMBO J., 6 pp. 643–649 (1987).
Parrkonen, et al., Biochem. J., 256 pp. 1005–1011 (1988).
Koivu et al. J. Biol. Chem., 262 pp. 6447–6449 (1987).
Geetha–Habib et al., Cell, 54 pp. 63–68 (1988).
Brockway & Freedman, Biochem. J., 219 51–59 (1984).
Freedman, Cell, 57 pp. 1069–1072 (1989).
Freedman et al., Biochem. Soc. Trans., 12 pp. 929–932 (1984).
Brockway et al., Biochem. J., 191 pp. 873–876 (1990).
Paver J.L. et al. FEBS Letters, 242 pp. 357–362 (1989).
Lambert & Freedman, Biochem. J., 213 pp. 225–234 (1983).
deAzevedo G.M.V. et al., Biochem. Soc. Trans., 12 pp. 1043 (1983).
George–Nascimento et al. (1988) Characterization of recombinant human epidermal growth factor produced in yeast. Biochemistry 27:797–802, Jan. 1988.*
Romanos et al. 91992) Foreign gene expression in yeast: a review. Yeast 8:423–488, Jun. 1992.*
Okumura et al. (1988), Agric. Biol. Chem. 52(7): 1735–1739.*
Han et al. (1989). Gene 75: 47–57.*
Neeper et al. (1990), J. Biol. Chem. 265(29): 17746–17752.*
Freedman, R.B. et al., Funct. of Gluthathione: Biochemical Toxicological and Clinical Aspects (Raven Press, New York), 1983, pp. 273–283.

\* cited by examiner

Primary Examiner—Robert A. Schwartzman
(74) Attorney, Agent, or Firm—J. Mark Hand; Jack L. Tribble

(57) ABSTRACT

Disclosed is a process for increasing the yield of disulfide bonded recombinant proteins produced by yeast, especially recombinant secreted proteins The enzyme protein disulfide isomerase (PDI) catalyzes the formation of disulfide bonds in secretory and cell-surface proteins. We disclose the construction of recombinant strains of the yeast *Saccharomyces cerevisiae* which overproduce either human PDI or yeast PDI in a regulated fashion. These strains show greatly increased secretion of disulfide bonded proteins of potential therapeutic significance. These strains have the potential to increase the production of various disulfide bonded proteins.

41 Claims, 13 Drawing Sheets

SEQUENCE LISTING

<160> NUMBER OF SEQ ID NOS: 23

<210> SEQ ID NO 1
<211> LENGTH: 6
<212> TYPE: PRT
<213> ORGANISM: Artificial Sequence
<220> FEATURE:
<223> OTHER INFORMATION: vertebrate PDI active site

<400> SEQUENCE: 1

Trp Cys Gly His Cys Lys
 1               5

<210> SEQ ID NO 2
<211> LENGTH: 4
<212> TYPE: PRT
<213> ORGANISM: Artificial Sequence
<220> FEATURE:
<223> OTHER INFORMATION: COOH-terminal sequence of S. cerevisiae PDI

<400> SEQUENCE: 2

His Asp Glu Leu
 1

<210> SEQ ID NO 3
<211> LENGTH: 6
<212> TYPE: PRT
<213> ORGANISM: Artificial Sequence
<220> FEATURE:
<223> OTHER INFORMATION: S. cerevisiae PDI thioredoxin active site

<400> SEQUENCE: 3

Trp Cys Gly Pro Cys Lys
 1               5

<210> SEQ ID NO 4
<211> LENGTH: 10
<212> TYPE: PRT
<213> ORGANISM: Artificial Sequence
<220> FEATURE:
<223> OTHER INFORMATION: thioredoxin-like active site

<400> SEQUENCE: 4

Phe Tyr Ala Pro Trp Cys Gly His Cys Lys
 1               5                  10

<210> SEQ ID NO 5
<211> LENGTH: 30
<212> TYPE: DNA
<213> ORGANISM: Artificial Sequence
<220> FEATURE:
<223> OTHER INFORMATION: oligonucleotide

<400> SEQUENCE: 5
cttacagtga ccacaccatg gagcgtagaa                                    30

<210> SEQ ID NO 6
<211> LENGTH: 26
<212> TYPE: DNA
<213> ORGANISM: Artificial Sequence
<220> FEATURE:
<223> OTHER INFORMATION: oligonucleotide

<400> SEQUENCE: 6
aattgcggcc gcaagcttgc ggccgc                                        26

```
<210> SEQ ID NO 7
<211> LENGTH: 26
<212> TYPE: DNA
<213> ORGANISM: Artificial Sequence
<220> FEATURE:
<223> OTHER INFORMATION: oligonucleotide

<400> SEQUENCE: 7
agctgcggcc gcaagcttgc ggccgc                                          26

<210> SEQ ID NO 8
<211> LENGTH: 15
<212> TYPE: DNA
<213> ORGANISM: Artificial Sequence
<220> FEATURE:
<223> OTHER INFORMATION: oligonucleotide

<400> SEQUENCE: 8
aattcgttga cgccc                                                      15

<210> SEQ ID NO 9
<211> LENGTH: 15
<212> TYPE: DNA
<213> ORGANISM: Artificial Sequence
<220> FEATURE:
<223> OTHER INFORMATION: oligonucleotide

<400> SEQUENCE: 9 tcggggcgt caacg                                                       15

<210> SEQ ID NO 10
<211> LENGTH: 73
<212> TYPE: DNA
<213> ORGANISM: Artificial Sequence
<220> FEATURE:
<223> OTHER INFORMATION: oligonucleotide

<400> SEQUENCE: 10
gatccacaaa acaaaatgct gcgccgcgct ctgctgtgcc tgccgtggtc cgccctggtg      60
cgcgccgacg ccc                                                        73

<210> SEQ ID NO 11
<211> LENGTH: 73
<212> TYPE: DNA
<213> ORGANISM: Artificial Sequence
<220> FEATURE:
<223> OTHER INFORMATION: oligonucleotide

<400> SEQUENCE: 11 tcggggcgt cggcgcgcac cagggcggac cacggcaggc acagcagagc gcggcgcagc       60
attttgtttt gtg                                                        73

<210> SEQ ID NO 12
<211> LENGTH: 88
<212> TYPE: DNA
<213> ORGANISM: Artificial Sequence
<220> FEATURE:
<223> OTHER INFORMATION: oligonucleotide

<400> SEQUENCE: 12
gatccacaaa acaaaatgaa gttttctgct ggtgccgtcc tgtcatggtc ctccctgctg      60
ctcgcctcct ctgttttcgc cgacgccc                                        88
```

<210> SEQ ID NO 13
<211> LENGTH: 88
<212> TYPE: DNA
<213> ORGANISM: Artificial Sequence
<220> FEATURE:
<223> OTHER INFORMATION: oligonucleotide

<400> SEQUENCE: 13 tcggggcgt cggcgaaaac agaggaggcg agcagcaggg aggaccatga caggacggca    60
ccagcagaaa acttcattt gttttgtg                                       88

<210> SEQ ID NO 14
<211> LENGTH: 91
<212> TYPE: DNA
<213> ORGANISM: Artificial Sequence
<220> FEATURE:
<223> OTHER INFORMATION: oligonucleotide

<400> SEQUENCE: 14
gacgacctcg aggacctcga agaagcagag gagccagaca tggaggaaga cgatgaccag    60
aaagctgtgc acgatgaact gtaaggatcc g                                  91

<210> SEQ ID NO 15
<211> LENGTH: 95
<212> TYPE: DNA
<213> ORGANISM: Artificial Sequence
<220> FEATURE:
<223> OTHER INFORMATION: oligonucleotide

<400> SEQUENCE: 15
aattcggatc cttacagttc atcgtgcaca gctttctggt catcgtcttc ctccgtatct    60
ggctcctctg cttcttcgag gtcctcgagg tcgtc                              95

<210> SEQ ID NO 16
<211> LENGTH: 31
<212> TYPE: DNA
<213> ORGANISM: Artificial Sequence
<220> FEATURE:
<223> OTHER INFORMATION: oligonucleotide

<400> SEQUENCE: 16
gatccacaaa acaaaatgaa gttttctgct g                                  31

<210> SEQ ID NO 17
<211> LENGTH: 31
<212> TYPE: DNA
<213> ORGANISM: Artificial Sequence
<220> FEATURE:
<223> OTHER INFORMATION: oligonucleotide

<400> SEQUENCE: 17
gcaccagcag aaaacttcat tttgttttgt g                                  31

<210> SEQ ID NO 18
<211> LENGTH: 51
<212> TYPE: DNA
<213> ORGANISM: Artificial Sequence
<220> FEATURE:
<223> OTHER INFORMATION: oligonucleotide

<400> SEQUENCE: 18
atatggatcc tgtctttgga taaaagacaa ggaccatttg gacccgggtg t             51

```
<210> SEQ ID NO 19
<211> LENGTH: 34
<212> TYPE: DNA
<213> ORGANISM: Artificial Sequence
<220> FEATURE:
<223> OTHER INFORMATION: oligonucleotide

<400> SEQUENCE: 19
tataggatcc ttatgataag cgtgggataa gctt                              34

<210> SEQ ID NO 20
<211> LENGTH: 20
<212> TYPE: DNA
<213> ORGANISM: Artificial Sequence
<220> FEATURE:
<223> OTHER INFORMATION: oligonucleotide

<400> SEQUENCE: 20
tacaaccgtc tgtgcatcaa                                              20

<210> SEQ ID NO 21
<211> LENGTH: 33
<212> TYPE: DNA
<213> ORGANISM: Artificial Sequence
<220> FEATURE:
<223> OTHER INFORMATION: oligonucleotide

<400> SEQUENCE: 21
actggatccg aattcaagct tagatgcaag cgt                               33

<210> SEQ ID NO 22
<211> LENGTH: 7
<212> TYPE: PRT
<213> ORGANISM: Artificial Sequence
<220> FEATURE:
<223> OTHER INFORMATION: portion of alpha-Factor Pre-Pro leader sequence
      (Figure 8)

<400> SEQUENCE: 22

Ile Leu Ser Leu Asp Lys Arg
 1               5

<210> SEQ ID NO 23
<211> LENGTH: 4
<212> TYPE: PRT
<213> ORGANISM: Artificial Sequence
<220> FEATURE:
<223> OTHER INFORMATION: portion of antistasin coding sequence
      (Figure 8)

<400> SEQUENCE: 23

Gln Gly Pro Phe
```

METHOD OF INCREASING PRODUCTION OF DISULFIDE BONDED RECOMBINANT PROTEINS BY SACCHAROMYCES CEREVISIAE

BACKGROUND OF THE INVENTION

Protein disulfide isomerase (PDI) is an enzyme involved in the catalysis of disulfide bond formation in secretory and cell-surface proteins. Using an oligonucleotide designed to detect the conserved "thioredoxin-like" active site of vertebrate PDI's (WCGHCK) (SEQ.ID.NO.: 1), we have isolated a gene encoding PDI from the lower eukaryote *Saccharomyces cerevisiae*. The nucleotide sequence and deduced open reading frame of the cloned gene predicts a 530 amino acid protein of molecular weight 59,082 and pI of 4.1, physical properties characteristic of mammalian PDIs. Furthermore, the amino acid sequence shows 30–32% identity and 53–56% similarity with mammalian and avian PDI sequences and has a very similar overall organization, namely the presence of two 100 residue segments, each of which is repeated, with the most significant homologies to mammalian and avian PDIs being in the regions (a, a') that contain the conserved "thioredoxin-like" active site. The N-terminal region has the characteristics of a cleavable secretory signal sequence and the C-terminal four amino acids (-HDEL)(SEQ.ID.NO.: 2) are consistent with the protein being a component of *S. cerevisiae* endoplasmic reticulum (E.R.). Transformants carrying multiple copies of this gene (designated PDI1) have 10-fold higher levels of PDI activity and overexpress a protein of the predicted molecular weight. The PDI1 gene is unique in the yeast genome and encodes a single 1.8 kb transcript that is not found in stationary phase cells, nor is it heat-inducible. Disruption of the PDI1 gene is haplo-lethal indicating that the product of this gene is essential for viability.

Protein disulfide-isomerase (PDI), an enzyme which catalyzes thiol:disulfide interchange reactions, is a major resident protein component of the E.R. lumen in secretory cells. A body of evidence on the enzymele cellular distribution, its subcellar location and its developmental properties suggests that it plays a role in secretory protein biosynthesis (Freedman, 1984, Trends Biochem. Sci. 9, pp.438–41) and this is supported by direct cross-linking studies in situ (Roth and Pierce, 1987, Biochemistry, 26, pp.4179–82). The finding that microsomal membranes deficient in PDI show a specific defect in cotranslational protein disulfide formation (Bulleid and Freedman, 1988, Nature, 335, pp.649–51) implies that the enzyme functions as a catalyst of native disulfide bond formation during the biosynthesis of secretory and cell surface proteins. This role is consistent with what is known of the enzyme's catalytic properties in vitro; it catalyzes thiol: disulfide interchange reactions leading to net protein disulfide formation, breakage or isomerization, and can catalyze protein folding and the formation of native disulfide bonds in a wide variety of reduced, unfolded protein substrates (Freedman et al., 1989, Biochem. Soc. Symp., 55, pp.167–192). The DNA and amino acid sequence of the enzyme is known for several species (Scherens, B. et al., 1991, Yeast, 7, pp. 185–193; Farquhar, R., et al., 1991, Gene, 108, pp. 81–89) and there is increasing information on the mechanism of action of the enzyme purified to homogeneity from mammalian liver (Creighton et al., 1980, J. Mol. Biol., 142, pp.43–62; Freedman et al., 1988, Biochem. Soc. Trans., 16, pp.96–9; Gilbert, 1989, Biochemistry 28, pp.7298–7305; Lundstrom and Holmgren, 1990, J. Biol. Chem., 265, pp.9114–9120; Hawkins and Freedman, 1990, Biochem. J., 275, pp.335–339). Of the many protein factors currently implicated as mediators of protein folding, assembly and translocation in the cell (Rothman, 1989, Cell 59, pp.591–601), PDI is unusual in having a well-defined catalytic activity.

PDI is readily isolated from mammalian tissues and the homogeneous enzyme is a homodimer (2×57 kD) with characteristically acidic pI (4.0–4.5) (Hillson et al., 1984, Methods Enzymol., 107, pp.281–292). The enzyme has also been purified from wheat and from the alga *Chlamydomonas reinhardii* (Kaska et al., 1990 Biochem. J. 268, pp.63–68). The activity has been detected in a wide variety of sources, and in a preliminary report, PDI activity was claimed to be detectable in *S. cerevisiae* (Williams et al., 1968, FEBS Letts., 2, pp.133–135). Recently, the complete amino acid sequences of a number of PDIs have been reported, largely derived from cloned cDNA sequences; these include the PDIs from rat (Edman et al., 1985, Nature, 317, pp.267–270) bovine (Yamauchi et al., 1987, Biochem. Biophys. Res. Comm., 146, pp.1485–1492) human (Pihlajaniemi et al., 1987, EMBO J., 6, pp.643–9), yeast (Scherens, B., et al., supra; Farquhar, R. et al., supra) and chick (Parkkonen et al., 1988, Biochem. J., 256, pp.1005–1011). The proteins from these vertebrate species show a high degree of sequence conservation throughout and all show several overall features first noted in the rat PDI sequence (Edman et al. 1985 supra). The most significant is the presence within the PDI sequence of two regions of approximately 100 residues strongly homologous to each other and closely related in sequence to thioredoxin, a small redox active-protein containing an active site disulfide/dithiol couple formed between vicinal Cys residues. In thioredoxin the active site sequence is WCGPCK (SEQ.ID.NO.: 3), whereas the corresponding region, found twice in PDI, has the sequence WCGHCK (SEQ.ID.NO.:1). (Other repeats, motif and homologies identified within the PDI sequences are discussed below).

Sequences corresponding to, or closely related to PDI have been identified in work aimed at analysing functions other than disulfide bond formation. For example, there is clear-cut evidence that PDI acts as the β subunits of the tetrameric $\alpha_2\beta_2$ enzyme prolyl-4-hydroxylase, which catalyzes a major post-translational modification of nascent or newly-synthesized procollagen polypeptides within the E.R. (Pihlajaniemi et al., 1987, supra; Koivu et al., 1987, J. Biol. Chem., 262, pp.6447–49)). There is also evidence suggesting that PDI participates in the system for cotranslational N-glycosylation (Geetha-Habib et al., 1988, Cell, 4, pp.63–68) and recently the proposal has been made that the enzyme participates in the complex which transfers triglyceride to nascent secretory lipoproteins (Wetterau at al., 1990, J. Biol. Chem., 265, pp.9800–7). Thus, PDI may be multi-functional in the co- and post-translational modification of secretory proteins (Freedman, 1989, Cell, 57, pp.1069–72).

The vast majority of mammalian secretory proteins contain multiple intramolecular and/or intermolecular disulfide bonds. Examples include, but are not limited to, pituitary hormones, interleukins, immunoglobulins, proteases and their inhibitors and other serum proteins. Such proteins are among the prime targets for commercial genetic engineering, but early experience in their expression in bacteria and yeast has highlighted a number of problems in obtaining them as functionally active recombinant products. This has drawn attention to the need for a better understanding of post-translational modifications in general, and of protein folding and disulfide bond formation in particular.

Disulfide bonded proteins comprising a single folded domain can, in general, be fully reduced and denatured and subsequently renatured in vitro to generate the correctly disulfide-linked state in reasonable yield. The process involves rapid formation of a mixed population of many differently disulfide bonded forms which slowly isomerize to give the native disulfide pairing. The process is catalysed by thiol/disulfide redox buffers (e.g. GSH and GSSG) and by alkaline pH. Low protein concentrations are required to prevent precipitation and interchain disulfide formation. In general the rate of formation of the native protein, and the optimal obtainable yield, both decrease as the number of intramolecular disulfides increases. The problem is compounded in proteins containing multiple disulfide bonded domains (e.g. tissue plasminogen activator) in which each domain must fold and form its native disulfide bonds independently.

The process of disulfide bond formation in vivo occurs co-translationally or as a very early post-translational event. Studies on nascent and newly synthesized secretory proteins in the lumen of the E.R. in mammalian cells show that native disulfide bonds are already formed. The process in vivo appears to be catalyzed by the enzyme protein disulfide-isomerase which is an abundant protein in secretory cells and is located at the luminal face of the endoplasmic reticulum [Freedman, R. B., 1984, Trends in Biochemical Sciences, 9, 438–441]. This enzyme in vitro, catalyzes thiol:protein-disulfide interchange reactions in a wide range of protein substrates and has the properties required of a cellular catalyst of native protein disulfide formation [Freedman, R. B. et al., 1984, Biochem. Soc. Trans., 12, 939–942]. Further evidence for its role include (i) that its tissue distribution matches that of the synthesis of disulfide bonded secretory proteins [Brockway, B. E. et al., 1980, Biochem, J., 191, 873–876], and (ii) that in a number of systems the amount of enzyme present varies in parallel with a physiological change in the rate of synthesis of disulfide bonded secretory protein [Brockway, B. E. et al., 1980, Biochem J., 191, 873–876; Freedman R. B. et al., 1983, in "Functions of Glutathione: Biochemical, Physiological, Toxicological & Clinical Aspects". eds. A. Larsson, S. Orrenius, A. Holmgren & B. Mannervik, Raven Press, New York, pp.271–282; Paver, J. L. et al., 1989, FEBS Letters, 242, pp. 357–362].

The enzyme has been characterized in a number of animal sources [Lambert, N. and Freedman, R. B., 1983, Biochem. J., 213, pp. 225–234], and in wheat [de Azevedo, G. M. V. et al., 1983, Biochem. Soc. Trans., 12, 1043], and a striking conservation of molecular and kinetic properties has been noted [Freedman, R. B. et al., 1984, Biochem. Soc. Trans. 12, pp. 939–942; Brockway, B. E. and Freedman, R. B., 1984, Biochem J., 219, 51–59]. However the enzyme has not been throughly studied in lower eukaryotes or in bacteria. The strong homologies between yeast and higher eukaryotes in the mechanisms and molecular components involved in secretion strongly suggest that the enzyme or an analogue is present in yeast, since at least some yeast secretory proteins (e.g. killer toxin) contain disulfide bonds.

The application of yeast as a versatile host for the expression of commercially-important mammalian proteins is compromised, to some extent, by the limited capacity of the yeast secretory system and by some differences between it and that of higher eukaryotes (e.g. in glycosylation).

The present invention provides a novel process for the production of disulfide bonded proteins in a recombinant host cell overexpressing the enzyme protein disulfide isomerase, and provides recombinant yeast cells which overexpress protein disulfide isomerase. The present invention also provides recombinant yeast host cells which substantially and unexpectedly increase the secretion of a recombinant disulfide bonded, secreted protein.

SUMMARY OF THE INVENTION

DNA encoding human and yeast protein disulfide isomerase (PDI) is isolated and cloned into expression casettes or vectors comprising a promoter and transcription terminator. The expression casettes or vectors containing PDI-encoding DNA are transferred into host cells which, as a result, overproduce PDI protein.

These PDI overproducing cells are used as recombinant hosts for the expression of disulfide bonded proteins. Secretion of disulfide bonded proteins is substantially increased in PDI overproducing host cells compared to host cells producing normal levels of PDI.

DETAILED DESCRIPTION OF THE INVENTION

Figure 1:
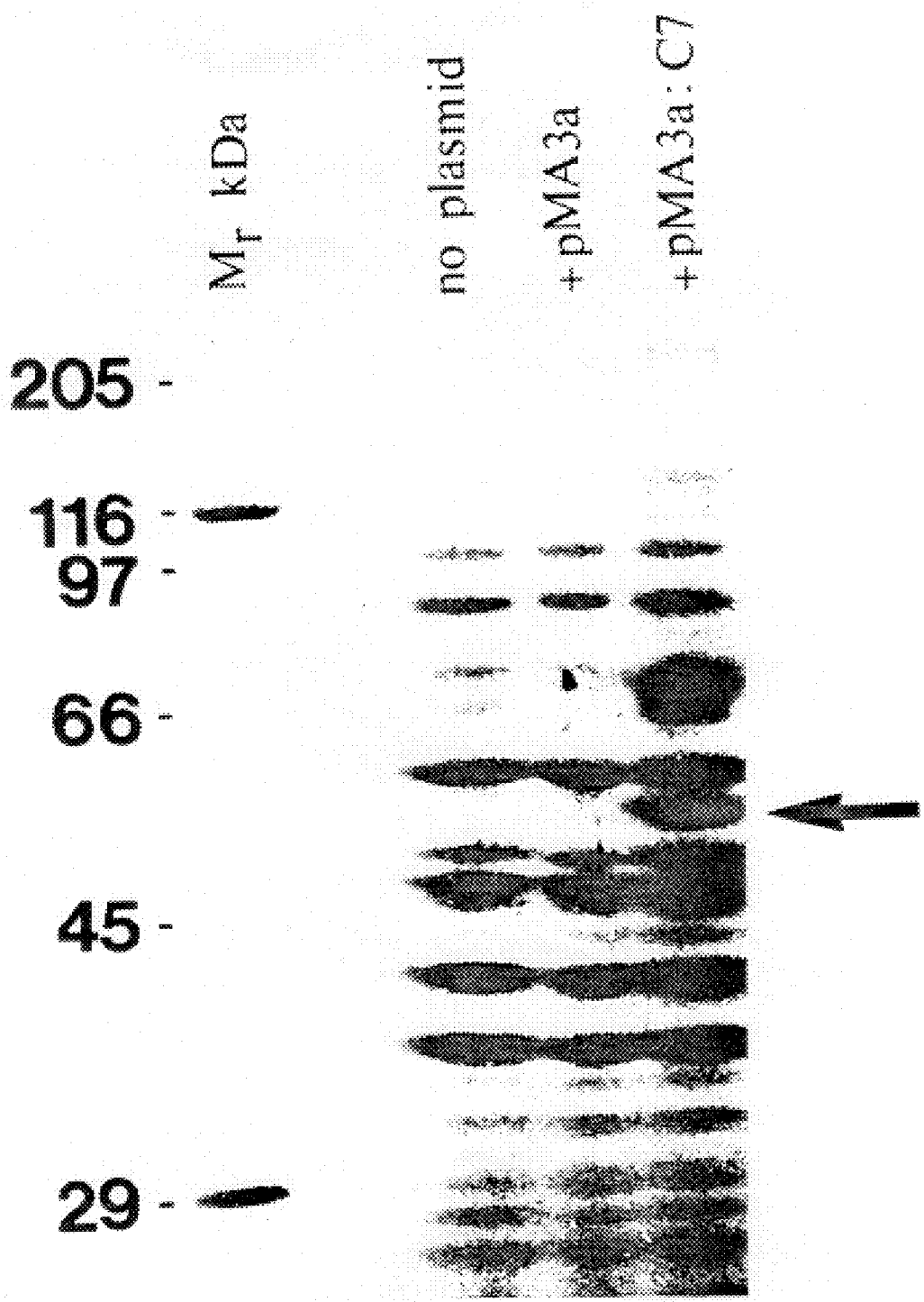
FIG. 1 shows the SDS-PAGE analysis of a cell-free lysate of an *S. Cerevisiae* transformant carrying a yeast PDI-encoding gene on a multicopy plasmid.

The process of protein folding and secretion in yeast is very complex, involving more than 30 gene products, based on genetic studies (Franzusoff, A. et al., 1991, Methods Enzymology, 194, pp. 662–674).

These include peptidyl prolyl cis-trans isomerases, PDI and other thioredoxin-like proteins, BiP, various molecular chaperones (hsp70, hsp60, etc.), signal peptidase, signal recognition protein, the various proteins involved in translocation of precursors into the E.R., the various structural and functional components of the ER, Golgi, and secretory vesicles plus many proteins not yet characterized (Franzuoff, A., et al., 1991, supra; Rothman, J. E. and Orci L., 1992, Nature, 355, pp. 409–415; Gething, M. G. and Sambrook, G., 1992, Nature, 355, pp. 33–45). In view of this complexity, it would seem very unlikely to one of ordinary skill in the art that increasing the levels of only one component (i.e. PDI) would be likely to substantially improve secretion of a particular heterologous protein. Therefore, the present invention provided very unexpected results in that increased levels of PDI alone caused a significant and substantial increase in the levels of secreted proteins, for example antistasin, a phenomenon which is likely to be related to improved protein folding and/or disulfide bond formation.

The present invention relates to a method for increasing the production of recombinant proteins by recombinant host cells, by overexpressing DNA encoding protein disulfide isomerase (PDI). PDI as used herein refers to an enzyme which specifically catalyzes the formation of intramolecular and intermolecular disulfide bonds.

The DNA sequence of PDI genes from several species is known in the art. These species include but are not limited to, human, bovine, rat, chicken and yeast. [Mizunaga et al., 1990, J. Biochem., 108, pp.846–851; Scherens et al., 1991, Yeast, 7, pp.185–193].

Starting material for the isolation of PDI-encoding DNA may be any cell or tissue type including but not limited to mammalian and other vertebrate cells and tissue, as well as lower eukaryotic cells and tissue The present invention is demonstrated using yeast and human PDI expressed in recombinant yeast host cells. It is readily apparent to one of ordinary skill in the art that the present invention extends to and encompasses other expression hosts including, but not limited to, mammalian cells, plant cells, prokaryotic cells such as bacteria, insect cells and lower eukaryotic cells such as yeast and filamentous fungi. Furthermore, it is readily apparent to one of ordinary skill in the art that the use of PDI encoding DNA derived from sources other than yeast and human cells is encompassed by the present invention. Other sources of PDI-encoding DNA include, but are not limited to, vertebrates other than human such as rat and mouse, non vertebrates such as insects, and lower eukaryotes such as fungi.

Microsomal membrane fractions prepared from *S. cerevisiae* by the method of Rothblatt and Meyer (1986, Cell, 44, pp.619–28) had low levels of protein disulfide isomerase (PDI) activity which were enhanced between 8–20 fold by sonication. This suggested the presence within the lumen of the yeast endoplasmic reticulum of an enzyme comparable to PDI found in the same cellular compartment in vertebrates (Mills et al., 1983, Biochem. J., 213, pp.245–8); Lambert and Freedman, 1985, Biochem., J. 228, pp.635–45) and wheat (Roden et al., 1982, FEBS Lett., 138, pp.121–4). The gene coding for PDI was cloned assuming homology to the higher eukaryotic enzymes. The region most likely to show strong conservation would be the a and a, domains which are highly conserved in vertebrate PDIs and show very strong homology to thioredoxin particularly in the region of the two functional dithiol active sites; the consensus sequence for the active site is FYAPWCGHCK (SEQ.ID.NO.: 4)(Parkonnen et al., 1988 supra). A nonredundant 30-mer oligonucleotide was designed based on yeast codon bias (Sharp at al., 1986, Nucleic Acids Res., 14, pp.5125–43) which was end-labelled and used to screen a yeast genomic library constructed in the multicopy YEp plasmid pMA3a (Crouzet and Tuite, 1987, Mol. Gen. Genet., 210, pp.581–3). Two strongly positive clones (designated C7 and C10) were recovered from the screen and preliminary restriction mapping revealed insert sizes of 14 kb and 14.5 kb, respectively, with the two inserts showing a number of restriction sites in common. The insert of clone C7 was further analysed.

To confirm that clone C7 did indeed encode PDI, the yeast *S. cerevisiae* strain MD40/4c [αtrp1 ura2 his3 leu2; Tuite et al., 1986, E.M.B.O.J., 1, pp.603–608] was transformed with clone C7 and with the parent plasmid pMA3a. SDS-PAGE analysis revealed that the C7 transformant overexpressed a major 58 kDa polypeptide and possibly a second polypeptide of approximately 77 kDa (FIG. 1). Furthermore, when the cell-free lysates of the two strains were assayed for PDI activity, the C7 transformant showed 10-fold higher levels of PDI activity ($38.6 \times 10^{-5}$ U/μg protein). These two lines of evidence supported the notion that the C7 clone encoded PDI and not thioredoxin since *S. cerevisiae* thioredoxin, which has the active site sequence WCGPCK (SEQ.ID.NO.: 3), has a molecular weight of approximately 12 kDa (Porque et al., 1970, J. Biol. Chem., 245, pp.2363–70).

To localise the putative PDI coding sequence, the C7 clone was digested with a variety of restriction enzymes, the digests transferred to nitrocellulose and probed with the 30-mer "active site" oligonucleotide described above. The procedure identified a 5 kb BamHI-SalI fragment and two apparently adjacent HindIII fragments of 5.0 and 4.5 kb respectively. The latter pattern suggested the possible existence of two targets for the "active site" probe as would be predicted for PDI which contains two copies of the active site. Preliminary DNA sequence analysis from the two HindIII sites revealed an open reading frame with weak homology to vertebrate PDIs, but also demonstrated that there must be a further HindIII site since they were not contiguous sequences. Detailed restriction mapping coupled with DNA sequencing confirmed this assumption. Using naturally occurring restriction sites and oligonucleotide primers a 2.5 kb HindIII-EcoRI fragment encompassing the two adjacent HindIII sites was sequenced on both strands.

Figure 2:
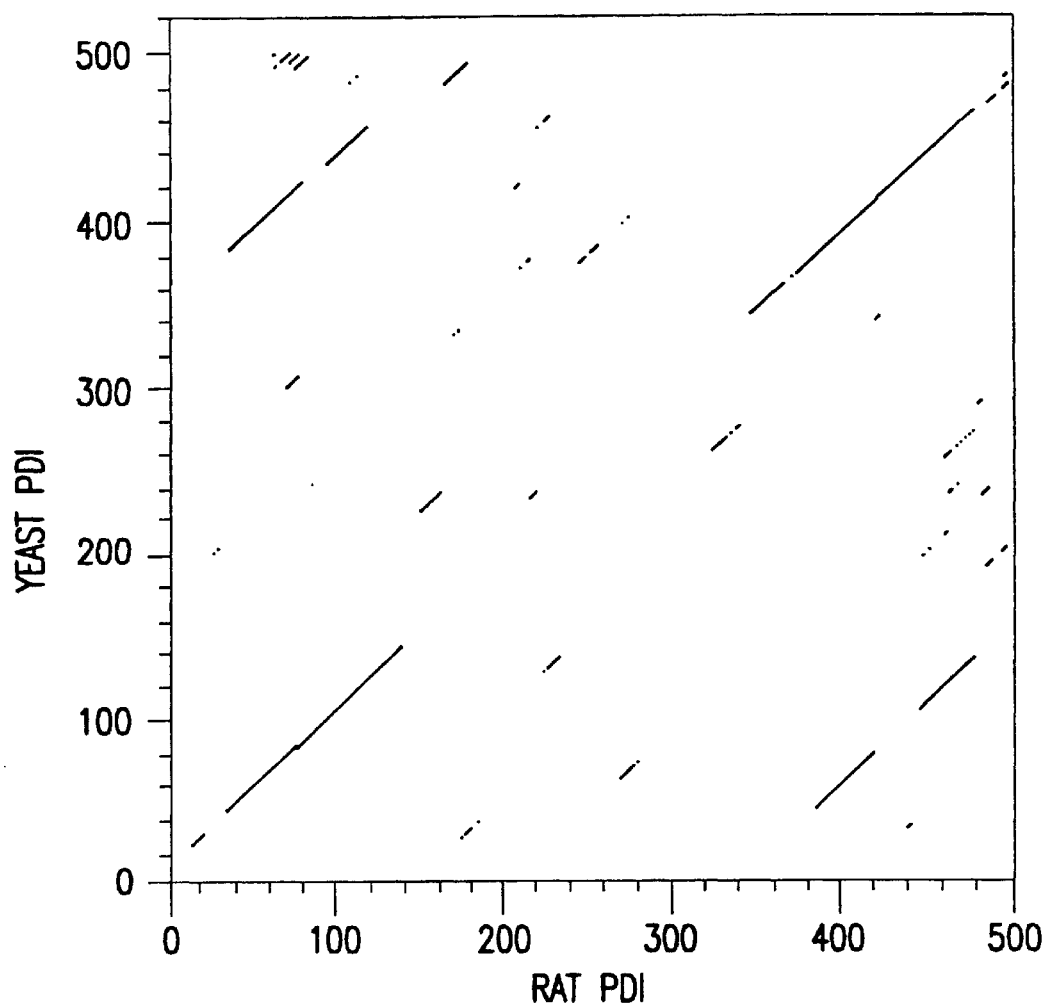
FIG. 2 shows the dot plot alignment between yeast PDI and rat PDI using the 'COMPARE' and 'DOTPLOT' software (UWGCG), the domain structure of mammalian PDI shown on the same scale and below the alignment.
Figure 2:

The DNA sequence predicted a single open reading frame of 1593 bp with the potential of encoding a polypeptide of 530 amino acids of predicted molecular weight of 59,082 (Farquhar, R., et al., supra, see FIG. 2). The open reading frame had a codon bias typical of yeast mRNAs that encode moderately abundant proteins (Bennetzen and Hall, 1982, J. Biol. Chem., 257, pp.3029–3031); the calculated codon bias index was 0.60.

Analysis of the determined nucleotide sequence reveals a number of standard yeast promoter and terminator motifs (Farquhar, R. et al., supra, see FIG. 2). These include a TATA box homology as part of a $(TA)_{14}$ sequence located between −100 and −128 relative to the open reading frame, and a pyrimidine rich region (34 out of 37 nucleotides) between position −201 and −238. At the 3' end of the open reading frame, following the TAA translational terminator there are homologies to both the sequence postulated to be a signal for transcription termination and/or polyadenylation in *S. cerevisiae* (Zaret and Sherman, 1982, Cell, 28, pp.563–73) and the eukaryotic polyadenylation site (Proudfoot and Brownlee, 1976, Nature, 264, pp.211–4).

To determine whether this cloned gene was transcribed, an 800 bp HindIII-StuI fragment internal to the open reading frame was used to probe a Northern blot of total RNA samples prepared from two different strains of *S. cerevisiae* (MD40/4c and SKQ2n [α/α ade1/+ade2/+his1/+; Gasion et al., 1979, J. Biol Chem., 254, pp.3965–3969]) grown on two different carbon sources, glucose and acetate, to different stages of the growth cycle. In exponentially growing cells a single 1.8 kb transcript was detected on glucose and acetate grown cells, while the transcript was barely detectable in non-growing cells. The size of the transcript was as predicted by the open reading frame allowing for approximately 200 nucleotides of non-translated sequence in 5' and 3' regions of the mRNA.

The predicted amino acid sequence strongly suggested that this was indeed PDI for the following reasons:

(i) it had a predicted molecular weight of 59 kDa and pI (4.1) characteristic of mammalian PDIs;
(ii) the amino acid sequence showed 30–32% overall identity and 53–56% overall similarity with previously reported mammalian and avian PDI sequences, as defined by BESTFIT software (UWGCG, University of Wisconsin); and
(iii) it contained two copies of the "thioredoxin-like" active site at positions 58–65 and 403–410 in the amino acid sequence. Furthermore, these sequences were part of larger internal duplications of approximately 100 amino acids which show strong amino acid identity with the duplicated a/a' regions within mammalian PDI (FIG. 2). Alignment of the yeast and mammalian PDI sequences also revealed other regions, outside the a and a' regions, which showed significant homology (FIG. 2).

In addition, two other features of the encoded polypeptide suggest it is a component of the *S. cerevisiae* endoplasmic reticulum; the protein encodes a very hydrophobic N-terminal sequence with the characteristics of a putative secretory signal (Gierasch, 1989, Biochemistry, 2, pp.923–930) and the four C-terminal amino acids are identical to those in yeast BiP (Normington et al., 1989, Cell, 57, pp.1223–36) and have been reported to be the endoplasmic reticulum retention signal for *S. cerevisiae* (Pelham et al., 1988, EMBO J., 7, pp.1757–62).

We have designated the cloned *S. cerevisiae* PDI gene PDI1. The *S. cerevisiae* PDI1 gene is present in only one copy in the genome. This was confirmed by high stringency hybridisation using the 0.8 kb HindIII-StuI fragment described above as a probe against a variety of genomic digests.

Figure 3A:
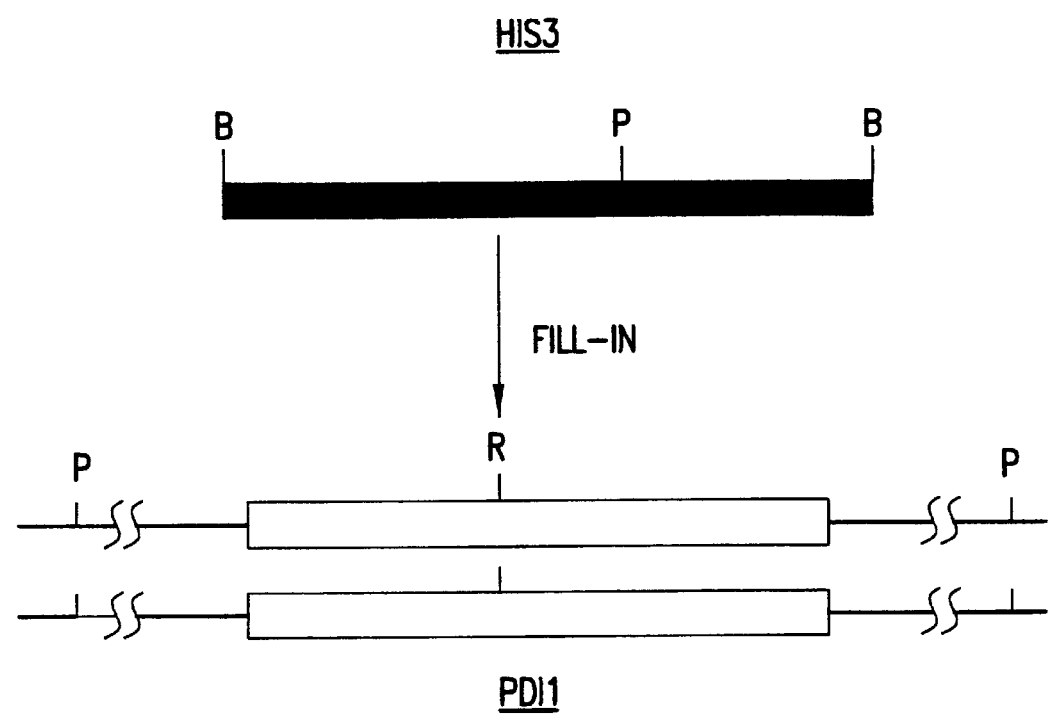
FIGS. 3A–3B depicts the strategy and shows results for disruption of the yeast PDI1 gene; Panel (b) shows the results for tetrad analysis of the His[+] AS3324 strain heterozygous for the pdi1::HIS3 disruption.
Figure 3B:
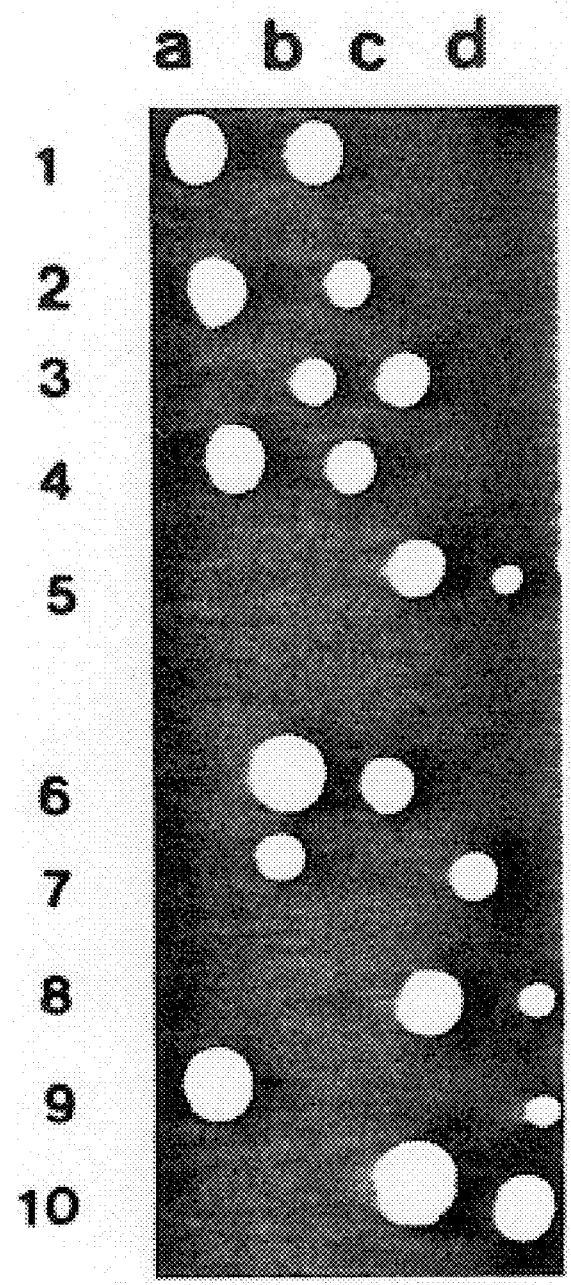

To determine whether the single PDI1 gene was essential for viability we constructed a null allele in which the 1.8-kb BamHI fragment carrying the HIS3 gene [Montiel, G. F. et al., 1984, Nucleic Acids Res., 12, pp.1049–1068] was inserted into the EcoRV site within the PDI1 coding sequence (FIG. 3). A his3 diploid yeast *S. cerevisiae* strain (AS3324; [Spalding, A., 1988, Ph. D. Thesis, University of Kent]) was transformed with a DNA fragment carrying the pdi1::HIS3 disruption to replace one of the two chromosomal copies of the PDI1 gene with this non-functional allele. Three HIS$^+$ AS3324 transformants (Y1, Y2 and Y3) were studied further and in each case sporulation of the diploids produced only two viable spores per tetrad (FIG. 3) all of which were his$^-$. This result indicates that the lethal phenotype was associated with pdi1::HIS3 mutation. That the correct gene replacement had arisen in the HIS$^+$ transformants Y1 and Y2 was confirmed by Southern hybridisation to blotted yeast genomic DNA digested with PstI using the 800 bp HindIII-StuI fragment as a probe. Since the PDI1 gene contains no internal PstI sites (FIG. 3) but the HIS3 gene does contain a single PstI site (FIG. 3) this should allow simple identification of the pdi1::HIS3 allele. As predicted in the untransformed strain AS3324, a single 9 kb PstI fragment was detected while in the Y1 and Y2 transformants two bands of 9 kb and 2.2 kb were detected with the 9 kb band presumably consisting of two bands of different origin. These data confirm that the PDI1 gene on one of the two chromosomes had been replaced with the HIS3 allele and that such an event was haplo-lethal.

Any of a variety of procedures may be used to molecularly clone yeast PDI-encoding DNA. These methods include, but are not limited to, direct functional expression of the PDI gene following the construction of a PDI containing DNA library in an appropriate expression vector system. Another method is to screen a PDI containing DNA library constructed in a bacteriophage or plasmid shuttle vector with a labelled oligonucleotide probe designed from the amino acid sequence of the PDI proteins. The preferred method consists of screening a human or yeast PDI-containing genomic DNA library constructed in a plasmid shuttle vector with a deduced DNA probe encoding the known amino acid sequence of the enzyme active site.

It is readily apparent to those skilled in the art that other types of libraries, as well as libraries constructed from other cells or cell types, may be useful for isolating PDI encoding DNA. Other types of libraries include, but are not limited to, cDNA and genomic DNA libraries derived from other human, vertebrate, invertebrate, and lower eukaryotic cells or cell lines, other than yeast cells.

It is readily apparent to those skilled in the art that suitable cDNA libraries may be prepared from cells or cell lines which have PDI activity. The selection of cells or cell lines for use in preparing a cDNA library to isolate PDI cDNA may be done by first measuring cell associated PDI activity using the procedures described fully above.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that PDI-encoding DNA may also be isolated from a suitable genomic DNA library.

Construction of genomic DNA libraries can be performed by standard techniques well known in the art. Well known genomic DNA library construction techiques can be found in Maniatis, T., Fritsch, E. F., Sambrook, J. in Molecular Cloning: A Laboratory Manuel (Cold Spring Harbor Laboratory, Cold Spring Harbor, N.Y., 1982).

The cloned PDI obtained through the methods described above may be recombinantly expressed by molecular cloning into an expression vector containing a suitable promoter and other appropriate transcription regulatory elements, and transferred into prokaryotic or eukaryotic host cells to produce recombinant PDI. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, fungi, insect cells and animal cells.

Specifically designed vectors allow the shuttling of DNA between hosts, such as between bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant PDI in mammalian cells. Commercially available mammalian expression vectors which may be suitable for recombinant PDI expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and gZD35 (ATCC 37565).

DNA encoding PDI may also be cloned into an expression vector for expression in a variety of recombinant host cells. Recombinant host cells may be prokaryotic, including but not limited to bacteria, or eukaryotic, including but not limited to yeast, mammalian cells including but not limited to cell lines of human, bovine, porcine, monkey and rodent origin, and insect cells including but not limited to Drosophila derived cell lines and *Spodoptera frugiperda* (SF9) insect cells for use with recombinant Baculovirus expression systems. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

A yeast active promoter initiates transcription of the PDI gene in yeast hosts. Therefore, it is readily apparent to those skilled in the art that any yeast-active promoter sequence may be used, including but not limited to, GAL1, GAL10, GAL7, PGK1, ADH1, ADH2, PHO5, and GAP491 (TDH3). It is also readily apparent to those skilled in the art that a suitable assay system, e.g., immunoblot or RIA or enzyme-linked immunoassay (EIA), may be utilized in order to assay expression of PDI in recombinant hosts.

*S. cerevisiae* has 5 genes which encode the enzymes responsible for the utilization of galactose as a carbon source for growth. The GAL1, GAL2, GAL5, GAL7, and GAL10 genes respectively encode galactokinase, galactose permease, the major isozyme of phosphoglucomutase, α-D-galactose-1-phosphate uridyltransferase and uridine diphosphogalactose-4-epimerase. In the absence of galactose, very little expression of these enzymes is detected. If cells are grown on glucose and then galactose is added to the culture, these three enzymes are induced coordinately, by at least 1,000-fold, (except for GAL5, which is induced to about 5 fold) at the level of RNA transcription. The GAL1, GAL2, GAL5, GAL7 and GAL10 genes have been molecularly cloned and sequenced. The regulatory and promoter sequences to the 5' sides of the respective coding regions have been placed adjacent to the coding regions of the lacZ gene. These experiments have defined those promoter and regulatory sequences which are necessary and sufficient for galactose induction.

*S. cerevisiae* also has 3 genes, each of which encodes an isozyme of ADH. One of these enzymes, ADHII, is responsible for the abiliy of *S. cerevisiae* to utilize ethanol as a carbon source during oxidative growth. Expression of the ADH2 gene, which encodes the ADHII isozyme, is catabolite-repressed by glucose, such that there is virtually no transcription of the ADH2 gene during fermentative growth in the presence of glucose levels of 0.1% (w/v). Upon glucose depletion and in the presence of non-repressing carbon sources, transcription of the ADH2 gene is induced 100- to 1000-fold. This gene has been molecularly cloned and sequenced, and those regulatory and promoter sequences which are necessary and sufficient for derepression of transcription have been defined.

Alpha mating factor is a sex pheromone of *S. cerevisiae* which is required for mating between MATα and MATa cells. This tridecapeptide is expressed as a prepropheromone which is directed into the rough endoplasmic reticulum, glycosylated and proteolytically processed to its final mature form which is secreted from cells. This biochemical pathway has been exploited as an expression strategy for foreign polypeptides. The alpha mating factor gene has been molecularly cloned and its promoter with pre-pro-leader sequence has been utilized to express and secrete a variety of polypeptides. Likewise, the PHO5 gene promoter has been shown to be inducible by low phosphate concentrations and this also has utility for physiologically regulated expression of foreign proteins in yeast.

The alpha mating factor promoter is active only in cells which are phenotypically α. There are 4 genetic loci in *S. cerevisiae*, known as SIR, which synthesize proteins required for the repression of other normally silent copies of a and α information. Temperature-sensitive (ts) lesions which interfere with this repression event exist in the gene product of at least one of these loci. In this mutant, growth at 35° C. abrogates repression, resulting in cells phenotypically a/α in which the alpha mating factor promoter is inactive. Upon temperature shift to 23° C., the cells phenotypically revert to α such that the promoter becomes active. The use of strains with a ts SIR lesion has been demonstrated for the controlled expression of several foreign polypeptides.

It is readily apparent to those skilled in the art that the selection of a suitable yeast strain for expression of PDI encompasses a wide variety of candidates. Suitable yeast strains include but are not limited to those with genetic and phenotypic characteristics such as protease deficiencies, and altered glycosylation capabilities.

The genus Saccharomyces is composed of a variety of species. *S. cerevisiae* is most commonly used as a host for the recombinant DNA-mediated expression of a variety of foreign polypeptides. However, the distinctions among other species of the genus Saccharomyces are not always well-defined. Many of these species are capable of interbreeding with *S. cerevisiae* and are likely to possess promoters which are analogous or identical to promoters in *S. cerevisiae*. Therefore, it will be readily apparent to those skilled in the art that, for the expression of PDI, the selection of a host strain extends to other species of the genus Saccharomyces, including, but not limited to, *carlsbergensis, diastaticus, elongisporus, kluyveri, montanus, norbensis, oviformis, rouxii*, and *uvarum*.

Several yeast genera such as Candida, Hansenula, Pichia, and Torulopsis have been shown to contain similar metabolic pathways for the utilization of methanol as a sole carbon source for growth. The gene for alcohol oxidase, an enzyme which participates in this metabolic pathway, has been isolated from *Pichia pastoris*. The *P. pastoris* alcohol oxidase promoter has been isolated and shown to be susceptible to methanol induction of expression. Such an inducible promoter is useful for expression of polypeptides in yeast. In particular, this promoter has been shown to be active on a plasmid for the inducible expression of heterologous genes in *P. pastoris*. This observation highlights the availability of other yeast genera to function as hosts for the recombinant DNA-mediated expression of polypeptides in active form. Therefore, it will be readily apparent to those skilled in the art that, for the expression of PDI, the selection of a host strain extends to species from other genera of yeast from the Families Saccharomycetaceae and Cryptococcaceae, including, but not limited to Candida, Hansenula, Kluyveromyces, Pichia, Saccharomyceopsis, and Torulopsis.

The expression vector may be introduced into host cells via any one of a number of techniques including but not limited to transformation, transfection, protoplast fusion, and electroporation. The expression vector-containing cells are clonally propagated and individually analyzed to determine whether they produce PDI protein. Identification of PDI expressing host cell clones may be done by several means, including but not limited to immunological reactivity with anti-PDI antibodies, and the presence of host cell-associated PDI activity.

Expression of PDI DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

It is readily apparent to those skilled in the art that PDI may be expressed in a recombinant host from a recombinant expression cassette which is integrated into the host cell genome, in single copy or multiple copies per cell. It is also readily apparent to those skilled in the art that PDI may be expressed in a recombinant host from a recombinant expression cassette which is present on an autonomously replicating plasmid in single copy or multiple copies per cell.

The recombinant host cell expressing recombinant PDI may be used, in turn, as a host for the expression of other recombinant genes. The novel process of the present invention substantially improves the yield of recombinant disulfide-bonded proteins by expressing the DNA encoding the recombinant disulfide-bonded proteins in a host cell which produces recombinant PDI. It is readily apparent to those skilled in the art that a variety of disulfide-bonded proteins may be produced by the process of the present invention. The disulfide-bonded proteins include, but are not limited to, proteins which are secreted, or remain cell-associated. Recombinant DNA constructs for the expression of recombinant disulfide-bonded proteins may be made by the procedures fully described above for PDI. It is readily apparent to those skilled in the art that the DNA encoding the recombinant disulfide-bonded proteins may be expressed from a recombinant expression cassette which is integrated into the host cell genome, in single copy or multiple copies per cell. It is also readily apparent to those skilled in the art that DNA encoding the recombinant disulfide-bonded protein may be expressed from a recombinant expression cassette which is present on an autonomously replicating plasmid in singly copy or multiple copies per cell. In addition, it is readily apparent to those skilled in the art that the DNA encoding PDI and the DNA encoding the recombinant disulfide-bonded proteins may be present on the same plasmid in single copy or multiple copies per cell. Furthermore, it is readily apparent to those skilled in the art that two or more disulfide bonded proteins may be co-expressed from either integrated or plasmid-borne cassettes, or a combination thereof.

Following expression of PDI in a recombinant host cell, PDI protein may be recovered to provide purified PDI in active form, capable of catalyzing the formation of disulfide bonds in proteins. Several PDI purification procedures are available and suitable for use. As described above for purification of PDI from natural sources, recombinant PDI may be purified from cell lysates and extracts, or from conditioned culture medium, by various combinations or individual application of salt fractionation, ion exchange chromatography, size exclusion chromatography, hydroxylapatite adsorption chromatography and hydrophobic interaction chromatography.

In addition, recombinant PDI can be separated from other cellular proteins by use of an immuno-affinity column made with monoclonal or polyclonal antibodies specific for PDI.

Monospecific antibodies to PDI are purified from mammalian antisera containing antibodies reactive against PDI or are prepared as monoclonal antibodies reactive with PDI using the technique of Kohler and Milstein, Nature 256: 495–497 (1975). Monospecific antibody as used herein is defined as a single antibody species or multiple antibody species with homogenous binding characteristics for PDI. Homogenous binding as used herein refers to the ability of the antibody species to bind to a specific antigen or epitope, such as those associated with PDI, as described above. Enzyme specific antibodies are raised by immunizing animals such as mice, rats, guinea pigs, rabbits, goats, horses and the like, with rabbits being preferred, with an appropriate concentration of PDI either with or without an immune adjuvant.

Preimmune serum is collected prior to the first immunization. Each animal receives between about 0.1 mg and about 1000 mg of PDI associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the enzyme in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with PDI are prepared by immunizing inbred mice, preferably Balb/c, with PDI. The mice are immunized by the IP or SC route with about 0.1 mg to about 10 mg, preferably about 1 mg, of PDI in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of PDI in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using PDI as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of PDI in body fluids or tissue and cell extracts.

It is readily apparent to those skilled in the art that the above described methods for producing monospecific antibodies may be utilized to produce antibodies specific for PDI polypeptide fragments, or full-length PDI polypeptide.

PDI antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing PDI are slowly passed through the column. The column is then washed with phosphate buffered saline until the optical density ($A_{280}$) falls to background, then the protein is eluted with 0.23 M glycine-HCl (pH 2.6). The purified PDI protein is then dialyzed against phosphate buffered saline.

The following Examples are provided as illustrative of the present invention, without, however, limiting the same thereto.

EXAMPLE 1
Strains and Growth Conditions

The *Saccharomyces cerevisiae* strains MD40/4C (MATα, leu2-3-112, ura2, his3-11,-15, trp1) and AS3324 (MATα/MAT"a" his3/his3, leu2/leu2, ura3/ura3, trp1/trp1) were grown at 30° C. in either YEPD (1% bactopeptone, 1% yeast extract, 2% glucose) or a pH5.8 buffered minimal medium (0.67% Yeast Nitrogen Base without amino acids, 2% glucose, 1% succinic acid, 0.6% NaOH, 50 μg/ml mesoinositol) supplemented with the necessary base and amino acid requirements.

The *S. cerevisiae* strains JRY188 (MATα, sir3-8, leu2-112, trp1, ura3-52, his4; Brake, A. J. et al., 1984, Proc. Nat'l. Acad. Sci. USA, 81, pp.4642–4646) and BJ1995 (MATα, leu2, trp1, ura3-52, prb1-1122, pep4-3, gal12; Jones, E. W., 1991, Methods Enzymol., 194, pp.428–453) were used for evaluation of PDI overexpression and were grown as described in the appropriate examples.

The *Escherichia coli* strain DH5α (supE44Δ1acU169 (φ801acZΔM15) hsdR17 recA1 endA1 gyrA96 thi-1 re1A1) was used for plasmid screening manipulations.

EXAMPLE 2
DNA Manipulation

Restriction endonuclease digests and DNA ligations were carried out as recommended by the enzyme manufacturers (BCL, BRL). Standard protocols for *E. coli* transformation (Cohen et al., 1972, P.N.A.S. USA, 69, pp.2110–9) and *S. cerevisiae* transformation (Beggs, 1978 Nature, 275, pp.104–9; Ito et al., 1983, J. Bacteriol., 153, pp.163–8) were performed. Genomic DNA was prepared from *S. cerevisiae* by the method of Holm et al. (1986, Gene, 42, pp.169–73).

EXAMPLE 3
Isolation of the PDI1 Gene

A yeast genomic library, containing partial Sau3A fragments of DNA from the *S. cerevisiae* strain SKQ2n [α/a ade1/+ade2/+his1/+; Gasion et al., Supra] cloned into the BamHI site of the high copy number LEU2-d, 2 micron-based vector pMA3a (Crouzet and Tuite, 1987, supra) was used to screen for the PDI1 gene. A 30-mer oligonucleotide (5'CTTACAGTGACCACACCATGGAGCGTAGAA 3') (SEQ.ID.NO.: 5) was synthesized against the highly conserved 'thioredoxin-like' active site (FYAPWCGHCK) (SEQ.ID.NO.: 4), but using a yeast codon bias (Sharp et al., 1986, supra).

To screen the library, 50 ng of the oligonucleotide was end-labelled with [γ-$^{32}$P]dATP [Amersham, 3000 Ci/mmol.] and T4 polynucleotide kinase, using DE-52 chromatography to separate the labelled oligonucleotide from unincorporated nucleotides. Approximately 20,000 DH5α recombinant colonies were screened on nitrocellulose filters by colony hybridisation as follows: each nitrocellulose filter was pre-hybridised for 16 hours at 37° C. in 35% formamide, 6×SSC, 1×Denhart's solution, 250 μg/ml denatured salmon sperm DNA, 0.1% SDS. The labelled oligonucleotide (specific activity $4.8 \times 10^9$ dpm/μg) was denatured for 3 minutes at 90° C. and then diluted to 2 ng/ml in prehydridisation buffer and added to the filters. After incubation at 37° C. for a further 16 hours the filters were removed and rinsed for 2 minutes in 4×SSC, 0.1% SDS. The filters were then autoradiographed overnight.

39 potential positive colonies were identified and taken through two further rounds of screening as described above, after which 10 positive clones (labelled C1 to C10) were obtained. Two of these clones (C7 and C10) were restriction mapped and clone C7 was chosen for subsequent studies.

EXAMPLE 4
DNA Sequence Anaylsis

To identify a suitable sized fragment for sequencing, clone C7 was digested with a range of restriction enzymes, and the fragments separated on a 1% agarose gel and transferred to Genescreen Plus membrane (DuPont) using a vacuum blotting apparatus (Hybaid Ltd.) The filter was then prehybridised essentially as described by Maniatis et al. 1982, supra, followed by the addition of the 30-mer oligonucleotide probe, end-labelled and denatured as described above. Hybridisation was carried out in 6×SSC for 24 hours at 43° C., followed by two washes in 200 ml of 2×SSC for five minutes at room temperature, two washes in 200 ml of 2×SSC 0.1% SDS for 1 hour at 65° C. and one final wash in 500 ml of 0.1×SSC at room temperature. The filter was then subject to autoradiography at −70° C. for 48 hours.

A 2.4 kb HincII-EcoRI fragment from clone C7 was completely sequenced using the dideoxy chain terminator method (Sanger et al., 1977, Proc. Nat'l. Acad. Sci. U.S.A., 74, 5463–67). Suitable restriction fragments for sequencing were subcloned into pUC19 and plasmid DNA prepared for sequencing using the rapid procedure of Holmes and Quigley (1981, Anal. Biochem., pp.193–7). In addition some fragments were cloned into the single-stranded vectors mp12 or mp13 (Messing, 1983, Methods Enzymol., 101, pp.20–78). A range of sequencing primers (15–18 mers) were synthesized which annealed either to the polylinker regions of the cloning vectors or to previously deduced internal C7 DNA sequences. Plasmid DNA was denatured prior to primer annealing in 0.2M NaOH, 2 mM EDTA for 30 minutes at 37° C., neutralised by the addition of 0.1 vol. 3M sodium acetate pH5.0 and precipitated with 3 vol. 95% ethanol at −70° C. for 15 minutes. T7 DNA polymerase (Sequenase, US Biochemicals) was used according to the manufacuturers' instructions for in vitro chain elongation, using [$\alpha$-$^{32}$P]dATP (3000 Ci/mmol;ICN) for labelling. Reactions were analysed as previously described (Bossier et al., 1989, Gene, 78, pp.323–30).

EXAMPLE 5
Preparation and Analysis of RNA

Total RNA was prepared from exponentially growing cells ($5\times10^6$–$1\times10^7$ cells/ml) or stationary phase cells ($2\times10^8$ cells/ml) of the strain MD40/4c. RNA was also extracted from exponentially growing cells of MD40/4c subjected to a 30 minute heat shock (30° C. to 42° C.). Total RNA was extracted essentially as described by Dobson et al., (1983, Nucleic Acids Res., 11, 2287–2302).

Northern blot analysis was carried out as follows: 20 μg total RNA was denatured in 20% formaldehyde 50% deionised formamide by heating at 55° C. for 15 minutes and then separated in a 1% agarose gel containing 8% formaldehyde. The RNA was transferred to a nitrocellulose filter (S&S, BA85) by vacuum blotting and the filter boiled in 10 mM Tris-HCl for 5 minutes. Hybridisation was carried out overnight at 42° C. in 10×Denhardts solution, 2×SSC, 50 mM phosphate buffer pH6.5, 40% formamide, 0.1% SDS, 400 μg/ml heat denatured salmon sperm DNA and 1–5 ng/ml of the probe. Filters were autoradiographed for 1–5 days at −70° C. Probes used were : a 0.8 kb HindIII-StuI fragment from the PDI1 gene (Farquhar, R. et al., supra, see FIG. 2) and plasmid Scp7 containing a portion of the 18S and 25S ribosomal RNA genes of S. cerevisiae cloned into pBR322 (obtained from Dr. B. S. Cox, University of Oxford). The probes were labelled by random primer labelling (BCL) according to the manufacturers' instructions.

EXAMPLE 6
Construction of a pdi1::HIS3 allele

A 1.8 kb BamHI fragment carrying the HIS3 gene was released from the plasmid pMA700 (Montiel et al., 1984, supra) and purified on 1% low melting point agarose (Sigma). The BamHI sticky ends of the fragment were filled in using dNTPs and the Klenow fragment of DNA polymerase I as described by Maniatis et al., 1982, supra. A 1.2 kb DraI-BglII fragment of the PDI1 gene was then subcloned into the SmaI-BamHI sites within the polylinker of the plasmid pUC19. Finally, the filled-in BamHI fragment containing the HIS3 gene was ligated into a unique EcoRV site within the PDI1 coding region (FIG. 3). The resulting pdi1::HIS3 allele was liberated on a 3.0 kb SalI-EcoRI fragment, purified on low melting agarose and used to transform the diploid strain AS3324 to His$^+$ prototrophy using the lithium acetate transformation protocol of Ito at al., (1983 supra).

EXAMPLE 7
In Vitro PDI Assay

The assay for PDI activity in total protein extracts was as described by Hillson et al., (1984, Methods Enzymol., 107, pp.281–92).

Preparation of Substrate

Scrambled ribonuclease is a fully oxidized mixture containing randomly formed disulfide bonds. It is prepared from commercially available (Sigma) bovine pancreatic ribonuclease A by the following method.

Incubate ribonuclease at 30 mg/ml (about 2.2 mM) in 50 mM TRIS-HCl buffer, pH 8.6, 8.9 M urea, 130 mM dithiothreitol (approximately 15-fold molar excess of dithiothreitol over reducible disulfide bonds) at ambient temperature for 18 to 20 hours, or at 35° C. for 1 hour.

Isolate reduced protein by acidification of the reaction mixture to pH 4 with glacial acetic acid, followed by immediate elution from a column of Sephadex G-25 with degassed 0.1M acetic acid. Monitor eluted fractions at 280 nm, pool protein-containing fractions, and estimate protein concentration either spectrophotometrically or chemically, using native ribonuclease A as the standard.

Dilute the sample of reduced ribonuclease to about 0.5 mg/ml with 0.1 M acetic acid. Add solid urea to give a final concentration of 10M, and sarcosine hydrochloride to 0.1M (sarcosine is included to react with cyanate ions that are present in concentrated solutions of urea and can inactivate ribonuclease by carbamylation). Adjust pH to 8.5 with 1M TRIS, and incubate at ambient temperature for 2 to 3 days in the dark, during which time the protein is randomly reoxidized by atmospheric $O_2$. After this incubation, determination of free thiol groups using 5,5'-dithiobis(2-nitrobenzoic acid) shows reoxidation to be complete (less than 0.1 free thiol per ribonuclease molecule).

Recover the scrambled product by acidification to pH 4 with glacial acetic acid and elution from Sephadex G-25 in 0.1 M acetic acid. Pool the fractions containing protein, adjust to pH 8 with 1 M TRIS, and store at 4° C.

The yield of scrambled ribonuclease through this procedure is typically 90–100%. The product is stable at 4° C. in solution for up to 6 months or, alternatively, may be dialyzed into 50 mM $NH_4.HCO_3$, pH 7.8, and then lyophilized, yielding a white fluffy solid that may be stored indefinitely at −20° C.

Assay Procedure

The substrate, scrambled ribonuclease, is essentially inactive in the hydrolytic cleavage of high-molecular-weight RNA, having about 2% of the activity of native ribonuclease. The action of PDI in catalyzing interchange of inter- and intramolecular disulfides in scrambled ribonuclease results in regain of the native disulfide pairing, native conformation and concomitant return of ribunuclease activity against RNA. Thus, the activity of PDI is assayed by a time-course incubation during which aliquots are removed and ribonuclease activity toward RNA is measured.

The sample of protein disulfide-isomerase is added to 50 mM sodium phosphate buffer, pH 7.5, to a final volume of 900 μl and preincubated with $10^{-5}$ M dithiothreitol (10 μl of 1 mM stock solution, made fresh daily) for 2 to 3 minutes at 30° C. TRIS-HCl buffer is also acceptable but gives about 25% lower activities. The assay is then started by the addition of a 100 μl aliquot of scrambled ribonuclease (0.5 mg/ml stock solution in 10 mM acetic acid, made fresh daily), and the incubation mixture is maintained at 30° C. For work on a smaller scale, the volumes above can be reduced 10-fold, to give a final assay volume of 100 μl. Aliquots of 10 μl are removed at 0.5 minutes and then at 2 to 3 minute intervals for up to 18 minutes, to assay for the reactivation of scrambled ribonuclease. Each aliquot is immediately added to an assay mixture of 3 ml of TKM buffer (50 mM TRIS-HCl buffer, pH 7.5, 25 mM KCl, 5 mM $MgCl_2$) containing 0.25 mg of highly polymerized yeast RNA (50 gl of 5 mg/ml stock solution), in a quartz cuvette previously equilibrated at 30° C. Ribonuclease activity is monitored at 30° C. using the dual-wavelength mode of a Perkin-Elmer 356 spectrophotometer (bandwidth 2.5 mm), and measuring change in $A_{260}$ relative to $A_{280}$ ($\Delta A$). The rate of RNA hydrolysis ($\Delta A$ min$^{-1}$) is constant over 1.5 to 2 minutes; a plot of this rate versus time of withdrawal of the aliquot from the incubation is linear for up to 15 minutes. The gradient of this linear portion of the time course ($\Delta A$ min$^{-1}$ min$^{-1}$) is calculated by linear regression analysis of triplicate assays (with correlation coefficient routinely $\geq 0.99$) and taken as a measure of protein disulfide-isomerase activity.

Control incubations are performed omitting enzyme sample to measure the rate of nonenzymatic reactivation of scrambled ribonuclease by dithiothretoil alone. These rates are usually less then $0.2 \times 10^{-3}$ $\Delta A$ min$^{-1}$ min$^{-1}$ and are subtracted in the calculation of the protein disulfide-isomerase activities of enzyme samples.

One unit of protein disulfide-isomerase activity is defined as the amount catalyzing reactivation of scrambled ribonuclease at a rate of one ribonuclease unit per minute; one ribonuclease unit is defined as the amount producing a change in $A_{260}$ relative to $A_{280}$ of 1 adsorbance unit per minute.

EXAMPLE 8
Construction of Vectors for Integration of PDI Expression Cassettes at Yeast LYS2 or URA3 Loci A vector was constructed for integration at LYS2 according to the following procedure. The plasmid pUC19 was digested with HindIII and the linear vector fragment was gel-purified. This fragment was then digested with EcoRI and the resulting 2.7 kbp EcoRI-HindIII vector fragment was gel-purified. The purified fragment was then ligated with the following synthetic oligonucleotide:

5'-AATTGCGGCCGCAAGCTTGCGGCCGC-3' (SEQ.ID.NO.: 6)

3'-CGCCGGCGTTCGAACGCCGGCGTCGA-5' (SEQ.ID.NO.: 7)

which contains an EcoRI cohesive end, NotI site, HindIII site, NotI site, and HindIII cohesive end, in that order. The resulting plasmid, pUC-Not, contains a unique HindIII site which is immediately flanked on both sides by NotI sites.

A plasmid for targetting of expression cassettes to integrate at the URA3 locus was constructed as described below. The source of the yeast URA3 gene was the 1.1 kbp HindIII fragment from YRp10 [Parent, S. A. et al., 1985, Yeast, 1, pp.83–138]. The plasmid pUC-Not was digested with HindIII, dephosphorylated with calf intestine alkaline phosphatase, and ligated with the 1.1 kbp HindIII URA3 fragment, yielding the plasmid pUC-Not-URA3.

A plasmid for targetting integration of expression cassettes to the LYS2 locus was constructed as follows. The plasmid YIp600 [Barnes, D. A. and Thorner, J., 1986, Mol. Cell. Biol., 6, pp.2828–2838] bearing the yeast LYS2 gene was digested with EcoRI plus HindIII and the 4.5 kbp EcoRI-HindIII fragment bearing the LYS2 gene was cloned into pUC19 which had been previously digested with EcoRI plus HindIII, yielding pUKC171. This plasmid was then digested with PvuII plus BglII and the 3.7 kbp PvuII-BglII fragment bearing the LYS2 gene was gel-purified and made flush-ended. Plasmid pUC-Not was digested with HindIII, dephosphorylated with calf intestine alkaline phosphatase, made flush-ended and then ligated with the 3.7 kbp LYS2 fragment. The resulting plasmid with the expected structure was designated pUC-Not-LYS2 (also called pNL).

A second vector for integration at LYS2 was also constructed. The plasmid YIp600 was digested with NcoI and the 3.0 kbp NcoI fragment bearing a major portion of the LYS2 protein coding sequence was gel-purified and made flush-ended. The plasmid pUC13 was digested with BamHI, made flush-ended, and ligated with the 3.0 kbp LYS2 fragment, yielding the integrating vector pUC13-LYS2.

EXAMPLE 9
Construction of Yeast Strains Which Overproduce Human PDI Fused to Yeast Alpha Factor Secretory Leader The source of the human PDI coding sequence was the overlapping partial cDNA clones p210 and p1 described by Pihlajaniemi et al. (1987, supra). The 0.45 kbp EcoRI-PstI fragment from p210 which carries the 5'-terminus of the human PDI cDNA was subcloned into pUC18, yielding plasmid pUKC150. Plasmid pUKC150 was then digested with EcoRI plus AvaI (AvaI cuts at the position corresponding to the third amino acid in the coding sequence for mature human PDI). The resulting 3.1 kbp vector backbone fragment was gel-purified and ligated with an oligonucleotide adapter having the structure:

5'-AATTCGTTGACGCCC-3' (SEQ.ID.NO.: 8)

3'-GCAACTGCGGGGCT-5' (SEQ.ID.NO.: 9)

This adapter reconstitutes the 5-end of the mature PDI coding sequence and contains a HindII site in such a position as to allow the precise fusion of the mature human PDI sequence to a desired secretory leader sequence.

Figure 4:
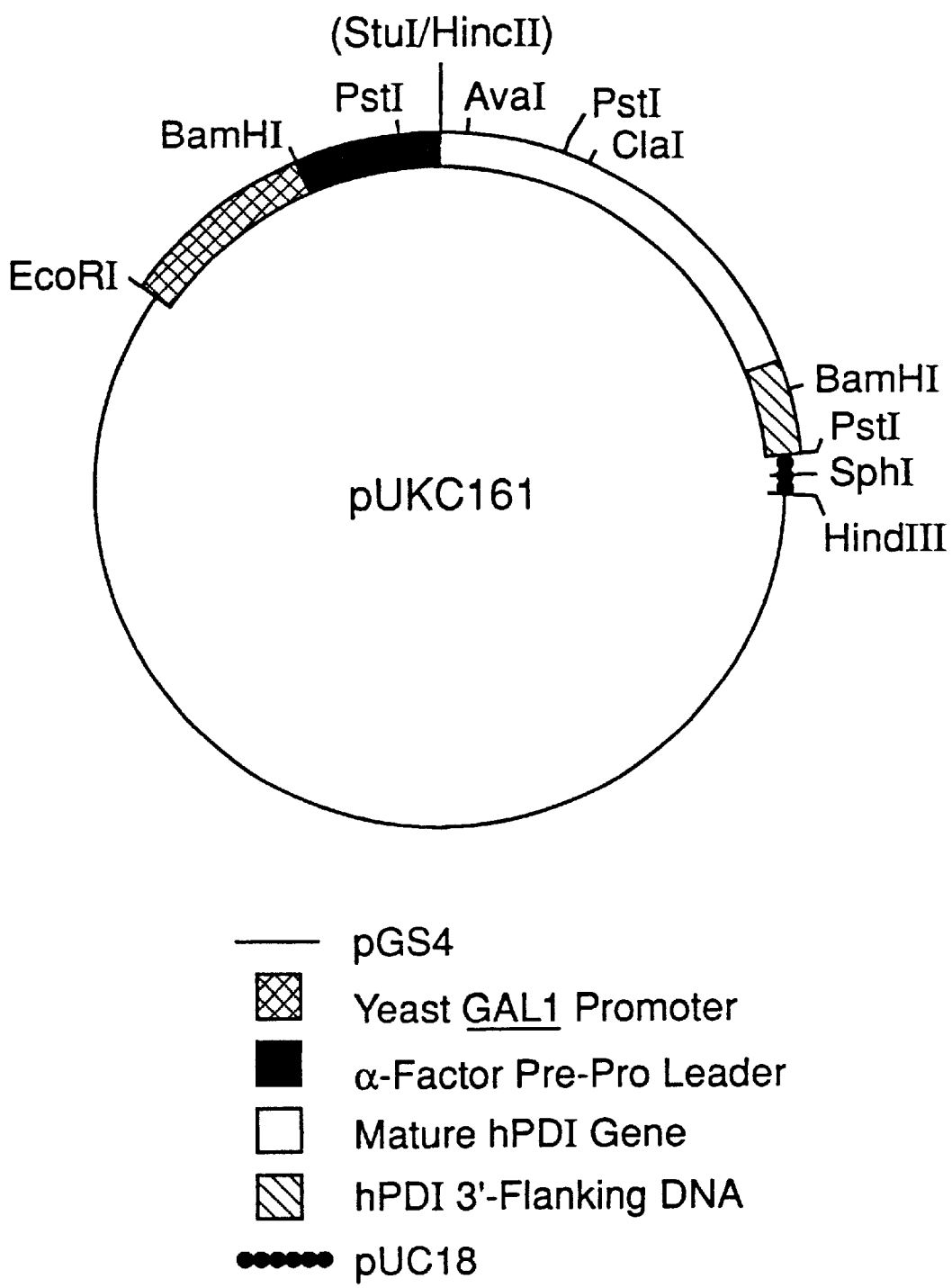
FIG. 4 shows the structure of plasmid pUKC161.

The resulting plasmid, pUKC159, was then digested with PstI, treated with calf intestine alkaline phosphatase, and ligated with the 1.5 kbp PstI-PstI fragment from plasmid pl (Pihlajaniemi et al., 1987, supra) which carries the remainder of the human PDI coding sequence, yielding plasmid pUKC160. Plasmid pUKC160 was then digested with HindII (which cuts within the aforementioned oligo adapter) followed by digestion with HindIII. The resulting 1.9 kbp HindII-HindIII fragment bearing the mature human PDI coding sequence was gel-purified and subcloned into plasmid pGS4 which had been previously digested with StuI plus HindIII (pGS4 carries the yeast GAL1 promoter fused to the alpha mating factor (MFα1) pre-pro secretory leader sequence; Shaw, K. J. et al., 1988, DNA, 7, 117–126). The junction formed between the blunt ended StuI and HindII termini reconstructs a precise in-frame fusion between the MFα1 pre-pro leader sequence and the mature portion of human PDI (resulting plasmid was designated pUKC161; FIG. 4).

The LYS2 integrating vector pNL (pUC-NotI-LYS2) was digested with StuI plus XhoI and made flush-ended by treatment with T4 DNA polymerase. Plasmid pUKC161 was digested with EcoRI plus HindIII and the resulting 2.8 kbp EcoRI-HindIII fragment bearing the GAL10 promoter—alpha factor pre-pro leader—human PDI expression cassette was gel-purified and made flush-ended by treatment with T4 DNA polymerase. The above flush-ended pNL vector fragment and this expression cassette fragment were ligated together and the ligation mixture was used to transform *E. coli* strain ATCC 35691. Transformants were screened for those containing a plasmid with the expected structure and the resulting plasmid, pNL-MFα1-hPDI was prepared in large amounts. When digested with NotI, pNL-MFα1-hPDI yields a 6.2 kbp expression cassette flanked on either end by LYS2 DNA sequences. The digested DNA was used to transform S. cerevisiae strains BJ1995 and JRY188 using the spheroplast method (Hinnen A. et al., 1978, Proc. Nat'l. Acad. Sci. USA, 75, pp.1929–1933). Acting as a targeting device, the NotI ends directed the expression cassette to the chromosomal LYS2 locus where the cassette integrated via homologous recombination. Transformants were screened for those which grow on solid media containing alpha-amino adipic acid (Chattoo, B. B. et al., 1979, Genetics, 93, pp.51; Barnes and Thorner, 1986, supra), indicating the strains are lys$^-$. Southern blot analysis of the clonal isolates using a LYS2 probe confirmed that the expression cassette had integrated at the LYS2 locus. Chromosomal DNA preparations digested with BglII showed the expected shift in size from 5.0 to 7.8 kbp for the band hybridizing with the LYS2 probe. The resulting BJ1995 and JRY188 related strains containing the integrated expression cassette were designated BJ1995/alpha-hPDI and JRY188/alpha-hPDI (strain #1072A) respectively.

EXAMPLE 10
Construction of Yeast Strains Which Overproduce Human PDI Using the Yeast PDI or Human PDI Signal Sequences The PDI cDNA clone pl (Pihlajaniemi et al., 1987, supra) was digested with PstI and the 1.5 kbp PstI-PstI fragment carrying the 3'-region of the human PDI cDNA was gel-purified. This fragment was then inserted into the PstI site of pUKC150 (described in Example 9 above) yielding the plasmid pUKC151, which contains the intact, full-length human PDI cDNA. pUKC151 was digested with HindIII and ligated with an appropriate oligonucleotide adapter (containing an EcoRI recognition sequence) to convert the HindIII site located at the 3'- end of the PDI cDNA to an EcoRI site. The resulting plasmid, pUKC153, contains the intact human PDI coding sequence on a 2.1 kbp EcoRI fragment. Plasmid pUKC153 was digested with EcoRI plus PstI. The resulting 0.47 kbp EcoRI-PstI and 1.7 kbp PstI-EcoRI fragments carrying the 5'- and 3'- portions of the human PDI sequence, respectively, were gel-purified. pUC19 was digested with EcoRI plus PstI and the 2.7 kbp vector fragment was gel-purified and then ligated with the aforementioned 0.47 kbp EcoRI-PstI fragment. The ligation mixture was used to transform E. coli ATCC 35691. Plasmid DNA was prepared from transformants containing a plasmid with the expected structure. This DNA was digested with AvaI plus PstI and a 0.38 kbp fragment carrying the 5'-portion of the human PDI sequence was gel-purified.

pUC19 was digested with EcoRI plus BamHI and the 2.7 kbp vector fragment was gel-purified. The following oligonucleotides were synthesized:

1. 5'-GATCCACAAAACAAAATGCTGCGC-
 CGCGCTCTGCTGTGCCTGCCGTGGTC-
 CGCCCTGGTGCGCGCCGACGCCC-3'
 (Oligo #15165-220) (SEQ.ID.NO.: 10)

2. 5'-TCGGGGGCGTCGGCGCGCACCAGGGCG-
 GACCACGGCAGGCACAGCAGAGCGCG-
 GCGGCAGCATTTTGTTTTGTG-3'
 (Oligo #15165-221) (SEQ.ID.NO.: 11)

3. 5'-GATCCACAAAACAAAATGAAGTTTTCT-
 GCTGGTGCCGTCCTGTCATGGTCCTC-
 CCTGCTGCTCGCCTCCTCTGTTTTCGCCGACGCCC-3'
 (Oligo #15165-249) (SEQ.ID.NO.: 12)

4. 5'-TCGGGGGCGTCGGCGAAAACAGAGGAG-
 GCGAGCAGCAGGGAGGACCATGACAG-
 GACGGCACCAGCAGAAAACTTCATTTTGTTTTGTG-3'
 (Oligo #15165-250) (SEQ.ID.NO.: 13)

Oligonucleotides #15165-220 and 15165-249 were kinased and then annealed with oligonucleotides #15165-221 and 15165-250, respectively. To reconstruct human PDI with the human PDI signal peptide sequence, the following ligation was set up: the pUC19 2.7 kbp BamHI-EcoRI fragment was ligated with the 1.7 kbp PstI-EcoRI hPDI 3'-fragment, the 0.38 kbp PstI-AvaI 5'-hPDI fragment, and the annealed linkers 15165-220 plus 15165-221.

To reconstruct human PDI with the yeast PDI signal sequence, the following ligation mixture was set up: the pUC19 2.7 kbp BamHI-EcoRI fragment was ligated with the 1.7 kbp PstI-EcoRI hPDI 3'-fragment, the 0.38 kbp PstI-AvaI 5'-hPDI fragment, and the annealed linkers 15165-249 plus 15165-250. (The annealed linkers contain BamHI and AvaI cohesive ends and encode the indicated signal peptide sequence plus yeast 5'-nontranslated leader sequence).

Figure 5:
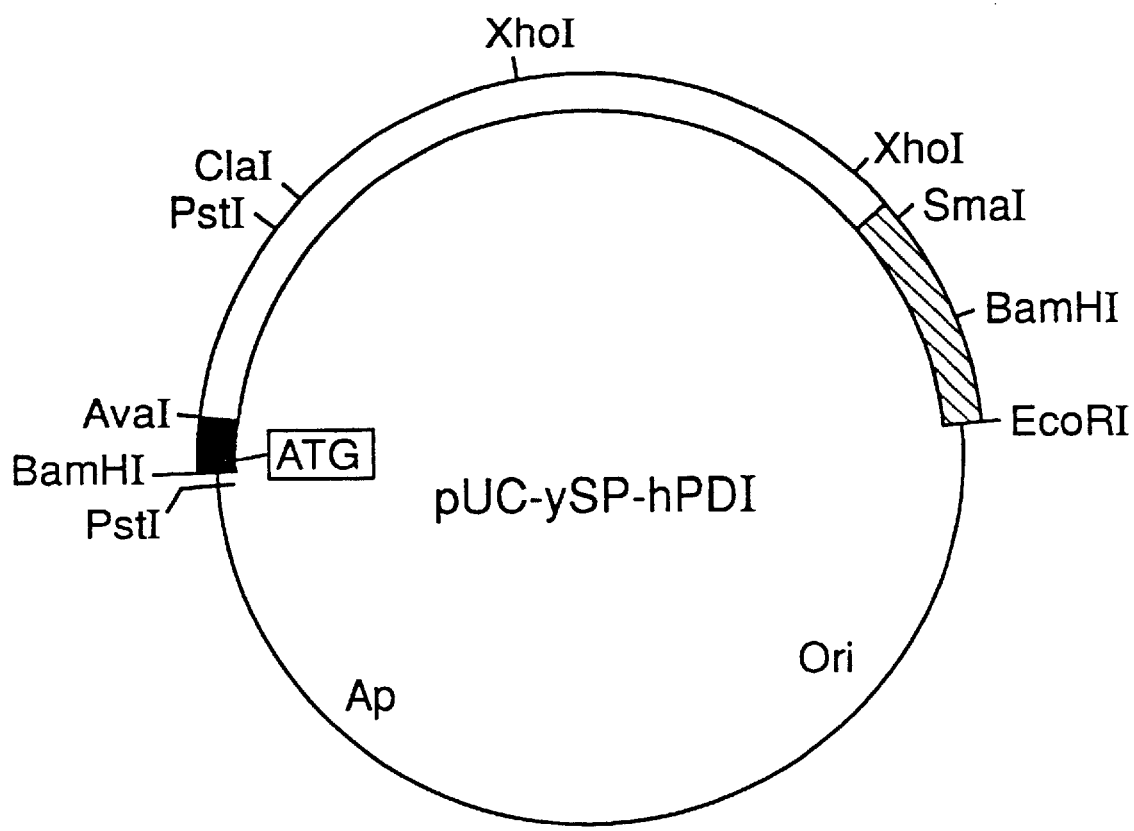
FIG. 5 shows the structure of plasmid pUC-ySP-hPDI.

The ligation mixtures were transformed into E. coli ATCC 35691 and transformants were screened for those containing plasmids with the expected structure. The DNA sequence across the region including the oligonucleotide linkers and the flanking DNA was confirmed by dideoxy sequencing methods. The human PDI coding sequences with either the yeast PDI signal peptide or human PDI signal peptide encoding sequences were designated ySP-hPDI and hSP-hPDI, respectively. The two resulting plasmids containing these cassettes (pUC-ySP-hPDI [FIG. 5] and pUC-hSP-hPDI, respectively) were digested with SmaI plus BamHI and the resulting 1.5 kbp fragments carrying the hPDI cassettes were gel-purified and made flush-ended.

Figure 6:
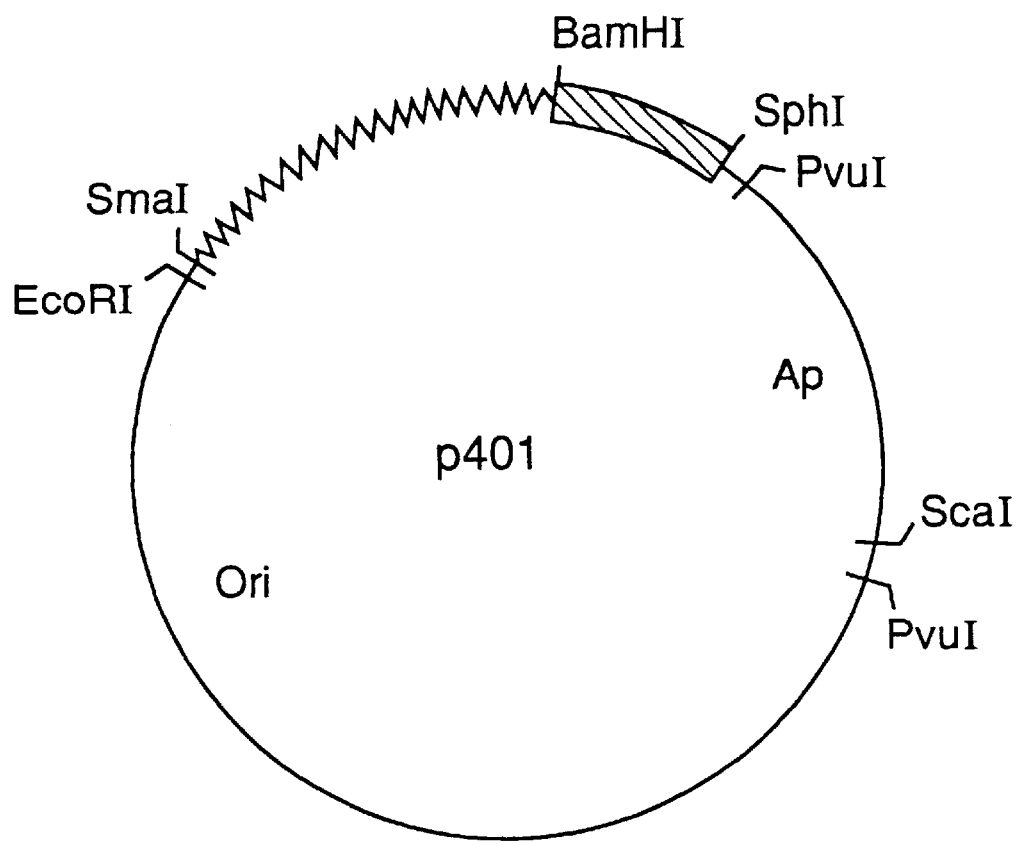
FIG. 6 shows the structure of plasmid p401, which is also known as pUC18-GAL10p(B)ADH1t.

The plasmid p401 (which contains the GAL10 promoter and ADH1 transcription terminator separated by a unique BamHI site; FIG. 6) was digested with BamHI, made flush-ended, and ligated with the aforementioned cassettes to yield the plasmids pGAL-ySP-hPDI and pGAL-hSP-hPDI, respectively. These two plasmids were digested with SmaI, SphI, and ScaI and the resulting 3.2 kbp SmaI-SphI fragments bearing the GAL10p-ySP-hPDI and GAL10p-hSP-hPDI expression cassettes were gel-purified, made flush-ended, and then inserted into the XhoI site (made flush-ended) of the LYS2 integrating vector, pUC13-LYS2. The resulting plasmids were designated pLYS2-hSP-hPDI and pLYS2-ySP-hPDI respectively.

For purposes of integrative transformation, these latter two plasmids were digested with XbaI plus SacI to generate linear fragments with LYS2 flanking ends and the linear fragments were used to transform yeast strains BJ1995 and JRY188. Transformants which had integrated the desired expression cassettes at LYS2 were identified by Southern blots of genomic DNA which had been digested with BglII and was then hybridized with a LYS2 probe. The resulting strains were BJ1995/hSP-hPDI, BJ1995/ySP-hPDI, JRY188/hSP-hPDI (strain #1148), and JRY188/ySP-hPDI (strain #1157).

EXAMPLE 11
Construction of Yeast Strains Which Overproduce a C-terminal HDEL Mutant of Human PDI Using the Human PDI or Yeast PDI Signal Peptide Yeast proteins which are resident in the endoplasmic reticulum normally contain a C-terminal HDEL amino acid sequence which is the signal for retention in the ER (Pelham, et al., 1988 supra). In contrast, human PDI has a C-terminal KDEL sequence (Pihlajaniemi, et al., 1987, supra) which has been previously shown to function poorly for ER retention in yeast (Lewis, M. J., et al., 1990, Cell, 61, pp.1359–1363). Therefore, it was desired to construct a modified human PDI in which the C-terminal KDEL was changed to HDEL. This was accomplished as follows.

The two plasmids pUC-ySP-hPDI and pUC-hSP-hPDI (Example 9) were digested with EcoRI and XhoI and the resulting 4.0 kbp EcoRI-XhoI fragment containing vector sequences plus the 5'-portion of the hPDI sequence and a 0.5 kbp XhoI-XhoI fragment containing the middle portion of the hPDI coding sequence were gel-purified. The following oligonucleotide adapter was then synthesized:

5'-GACGACCTCGAGGACCTCGAAGAAGCA-
   GAGGAGCCAGACATGGAGGAA

3'-CTGCTGGAGCTCCTGGAGCTTCT-
   TCGTCTCCTCGGTCTATGCCTCCTT

GACGATGACCAGAAAGCTGTGCACGAT-
   GAACTGTAAGGATCCG-3'                    (SEQIDNO.:14)

CTGCTACTGGTCTTTCGACACGTGC-
   TACTTGACATTCCTAGGCTTAA-5'              (SEQIDNO.: 15)

Following annealing of the two oligos, this adapter was digested with XhoI (now yielding EcoRI and XhoI cohesive ends) and ligated in two separate reactions with the 4.0 kbp EcoRI-XhoI vector fragments containing either the 5'-ySP-hPDI or 5'-hSP-hPDI sequences, respectively. The resulting two plasmids were then digested with XhoI and ligated with the aforementioned 0.5 kbp XhoI-XhoI fragment containing the middle portion of the hPDI coding sequence, yielding the plasmids pUC-ySP-hPDI(HDEL) and pUC-hSP-hPDI (HDEL), respectively, into which the XhoI fragment had inserted in the correct orientation to reconstruct the human PDI coding sequence. These two plasmids were then digested with BamHI and the two different 1.5 kbp BamHI fragments carrying the expression cassettes were gel-purified and then inserted into the BamHI site of p401, yielding pUC-GAL10p-ySP-hPDI(HDEL) and pUC-GAL10p-hSP-hPDI(HDEL), respectively. These two plasmids were then digested with SmaI, SphI and PvuI. The resulting two 2.5 kbp SmaI-SphI fragments were gel-purified, made flush-ended and then ligated with pUC13-LYS2 which previously had been digested with XhoI and made flush-ended. The resulting two plasmids, pLYS2-ySP-hPDI(HDEL) and pLYS2-hSP-hPDI(HDEL) were linearized by digestion with HpaI plus EcoRV and then used in separate reactions for transformation of strains BJ1995 and JRY188. Lys⁻ transformants were selected on solid media containing alpha-amino adipic acid. Isolates containing the desired expression cassette integrated at the LYS2 locus were identified by Southern blot analysis of genomic DNA. The resulting strains were designated BJ1995/ySP-hPDI (HDEL), BJ1995/hSP-hPDI(HDEL), JRY188/ySP-hPDI (HDEL) (strain #1268), and JRY188/hSP-hPDI(HDEL) (strain #1267).

EXAMPLE 12
Construction of Yeast Strains Which Overproduce C-terminal HDEL Mutant of Human PDI Using the Yeast Alpha Factor Secretory Leader Plasmid pUKC161 (FIG. 4) was digested with BamHI plus ClaI and the 0.7 kbp BamHI-ClaI fragment bearing the alpha factor pre-pro leader sequence and 5'-segment of hPDI was gel-purified. The plasmid pUC-ySP-hPDI(HDEL) (described in Example 11) was digested with ClaI and EcoRI and the 1.0 kbp ClaI-EcoRI fragment bearing the 3'-segment of hPDI with the C-terminal HDEL modification was gel-purified. pUC19 was digested with BamHI plus EcoRI and the resulting vector fragment was ligated with both the 0.7 kbp BamHI-ClaI fragment and the 1.0 kbp ClaI-EcoRI fragment to yield the plasmid pUC-MFα1-hPDI(HDEL). This plasmid was digested with BamHI and the 1.7 kbp BamHI-BamHI fragment carrying the PDI cassette was gel-purified and inserted into the BamHI site of the plasmid p401 (FIG. 6), yielding the plasmid pGAL-MFα1-hPDI (HDEL). This plasmid was then digested with the enzymes SmaI, SphI, and PvuI and the resulting 2.6 kbp SmaI-SphI fragment bearing the expression cassette was gel-purified and made flush-ended. The pUC13-LYS2 vector was digested with XhoI, made flush-ended and then ligated with the above 2.6 kbp flush-ended fragment. The resulting plasmid, pLYS2-MFα1-hPDI(HDEL) was digested with HpaI plus EcoRV and then used for transformation of strains JRY188 and BJ1995. The resulting transformants were evaluated by Southern blots of genomic DNA (as described in Example 9) to confirm that the desired expression cassette had integrated at the LYS2 locus. The JRY188 transformant was designated strain #1279.

EXAMPLE 13
Construction of Yeast Strains Which Overexpress the Yeast PDI Protein from an Integrated Expression Cassette at LYS2 Locus The plasmid C7 (described in Example 4) bearing the complete yeast PDI1 gene was digested with EcoRV and the 1.3 kbp EcoRV-EcoRV fragment containing the C-terminal portion of the yeast PDI open reading frame (ORF) (from amino acid 223 to end of ORF) plus the 3'-nontranslated sequence was gel-purified and inserted into the EcoRV site of the plasmid pAT153 [Twigg, A. G. and Sherratt, D., 1980, Nature, 283, pp.216–218], yielding pUKC169. Plasmid C7 was then digested with BanI plus EcoRV and the 0.67 kbp BanI-EcoRV fragment encoding amino acids 6–222 of the yeast PDI ORF was gel-purified and ligated with the following synthetic oligonucleotide adapter:

5'-GATCCACAAAACAAAATGAAG
   TTTTCTGCTG-3'                          (SEQ.ID.NO.: 16)

3'-GTGTTTTGTTTTACTTCAAAAG
   ACGACCACG-5'                           (SEQ.ID.NO.: 17)

which contains BamHI and BanI cohesive ends, respectively, and encodes amino acids 1–5 of the yeast PDI ORF plus 12 basepairs of yeast 5'-nontranslated leader sequence. (The ATG initiation codon is underlined.) The resulting 0.7 kbp BamHI-EcoRV fragment was gel-purified and then subcloned into pAT153 which had been previously digested with EcORV plus BamHI, yielding the plasmid pUKC170.

Figure 7:
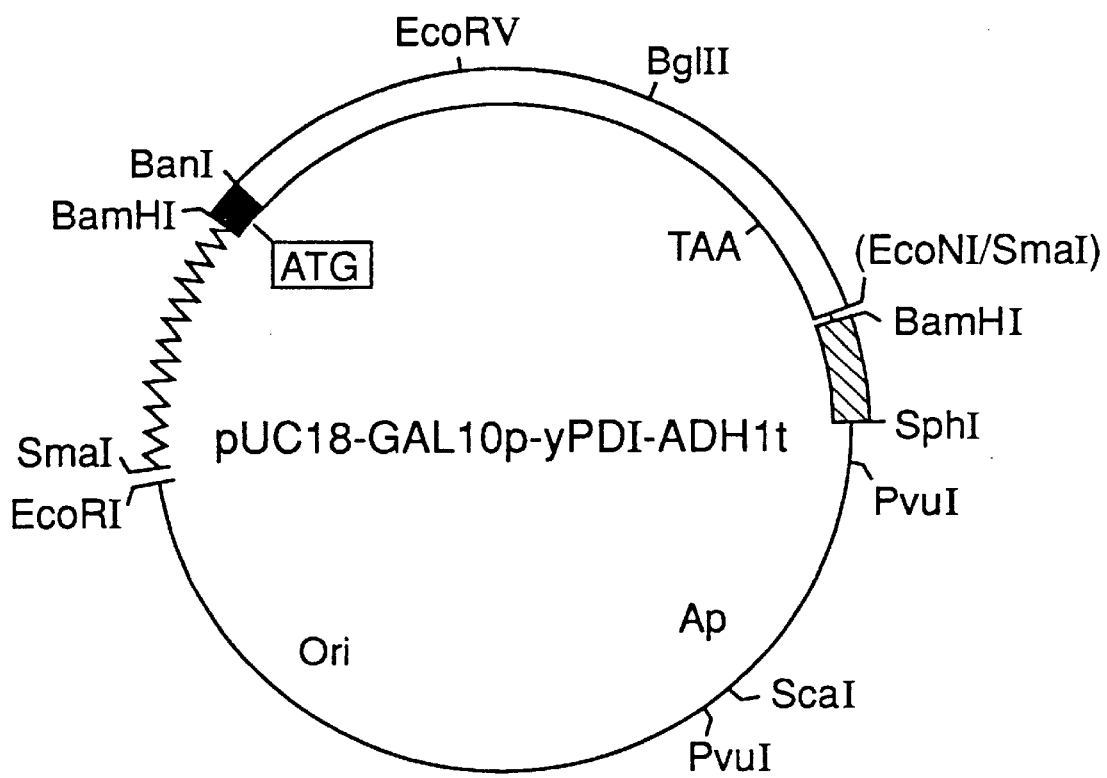
FIG. 7 shows the structure of the plasmid pUC18-GAL10p-yPDI-ADH1t.

Plasmid pUKC169 was digested with EcoRV and the resulting 1.3 kbp EcoRV-EcoRV fragment bearing the aforementioned C-terminal portion of yeast PDI was gel-purified and then inserted into the unique EcoRV site of pUKC170 thereby regenerating the intact yeast PDI (yPDI) gene. This resulting plasmid was designated pUKC175.

pUKC175 was digested with EcoNI and the resulting 2.1 kbp fragment bearing the yPDI gene was made flush-ended and gel-purified. pUC19 was digested with SacI plus SmaI, made flush-ended, and ligated with the above flush-ended EcoNI yPDI fragment. The ligation mixture was used to transform E. coli DH5 cells and the resulting transformants were screened for those containing plasmids with the yPDI insert in the appropriate orientation such that a BamHI site in the pUC19 polylinker was located adjacent to the 3'-end of the yPDI coding sequence. As a BamHI site already existed at the 5'-end of the yPDI ORF on the EcoNI fragment, this construct (designated pUC19-yPDI) now contains the yPDI ORF on a 1.9 kbp BamHI fragment. pUC19-yPDI was digested with BamHI and the 1.9 BamHI kbp fragment bearing the yPDI gene was gel-purified and then subcloned into the BamHI site of the vector pUC18-GAL10p(B)ADH1t (stock #401) (FIG. 6). The resulting plasmid, pUC18-GAL10p-yPDI-ADH1t (FIG. 7), is stock #1015. Plasmid pUC18-GAL10p-yPDI-ADH1t was digested with SmaI, SphI, plus SacI and the 2.7 kbp SmaI- SphI fragment carrying the expression cassette was gel-purified, made flush-ended, and then cloned into the unique StuI site of pUKC171 (pUKC171 contains the 4.5 kbp EcoRI-HindIII LYS2 fragment of YIp600 (Barnes and Thorner, 1986, supra) subcloned into pUC19 which had been previously digested with EcoRI plus HindIII). The resulting pUKC171-GAL10p-yPDI vector was then digested with EcoRI plus PvuII to excise the LYS2-GAL10p-yPDI-ADH1t-LYS2 cassette which was then used to transform *S. cerevisiae* strains JRY188 and BJ1995. The resulting lys⁻ transformants were evaluated by Southern blots of genomic DNA preparations as described in Example 9. Isolates of each strain were found which had the GAL10p-yPDI cassette integrated at the LYS2 locus. The resulting strains were designated BJ1995/yPDI and JRY188/yPDI (strain #1152).

EXAMPLE 14
Construction of a Yeast Strain Which Overproduces Yeast PDI From an Integrated Expression Cassette at URA3 Locus The plasmid pUC-Not-URA3 (Example 8) was digested with ApaI plus NcoI (to delete a portion of the URA3 gene) and made flush-ended. Plasmid pUC18-GAL10p-yPDI-ADH1t was digested with EcoRI, ScaI, and SphI and the 2.8 kbp EcoRI-SphI fragment bearing the GAL10p-yPDI-ADH1t expression cassette was gel-purified, made flush-ended, and ligated with the above vector fragment, yielding the plasmid pNU-GAL10p-yPDI. The URA3-GAL10p-yPDI-ADH1t-URA3 integrating cassette was excised from pNU-GAL10p-yPDI by digestion with NotI. The resulting linear fragment was used to transform yeast strain KHY107. Ura⁻ transformants were selected on solid media containing 5-fluoro-orotic acid (Boeke et al., 1984, Mol. Gen. Genet., 197, pp 345). Genomic DNA from the resulting ura⁻ transformants was digested with BglII and evaluated by Southern blots using a radiolabelled EcoRI-PvuII fragment from the GAL10p-yPDI-ADH1t cassette as probe. Isolates were identified which had integrated the desired GAL10p-yPDI-ADH1t expression cassette at URA3. Isolate K-Y1 had multiple copies integrated at URA3 (strain #1136). Isolate K-Y3 had one copy integrated at URA3 (strain #1137).

EXAMPLE 15
Evaluation of PDI Protein Levels In Recombinant Hosts

Yeast strains were grown in 3×YEPD liquid medium for 24 hours, at 23° C. After that period, cultures were supplemented with galactose to a final 4.8% concentration. The cultures were then reincubated at 23° C., for an additional period of 24 hours. Alternatively, yeast strains were cultivated in 3×YEPD for 24 hours at 30° C. The cells were harvested and washed with cold sterile water, and resuspended in the same volume of 3×YEPD-Galactose medium. The yeast strains were incubated for a further period between 16 and 25 hours, after which, they were harvested and protein extracted by extraction method 2 (below).

Protein Extraction

Proteins were extracted from exponentially growing or stationary phase cells using glass bead disruption, essentially as described by Mellor et al., (1983, Gene, 24, pp.1–14).

Method 1

Protein was extracted by glass bead disruption of cell walls, in the presence of PMSF (0.5 mM) in a 25 mM phosphate buffer pH 7.0, followed by a freeze-thaw cycle, and soluble protein was recovered by centrifugation for 10 minutes at 13,000 rpm. Secretion was initially assessed by analysis of spent culture liquid, either before or after concentration with PEG (solid), ammonium sulphate (0–80%), or an ultrafiltration membrane (<100 kDa). Protein concentration was determined by the method of Bradford (1976, Anal. Biochem., 72, pp. 248–254).

Method 2

Intracellular samples were prepared as in method 1, but the culture medium was supplemented with NaOH, and β-mercaptoethanol (respectively, final concentrations of 0.2M and 1%), left on ice for about 10 minutes, after which TCA was added to a final concentration of 6%. After 30 minutes standing on ice, protein was recovered by centrifugation, washed with cold acetone and resuspended in SDS-PAGE loading buffer.

50 μg of total soluble protein was analysed by one dimensional SDS-PAGE (12% polyacrylamide) and Coomassie blue staining essentially as described by Schultz et al., (1987, Gene, 54, pp.113–23).

Electrophoresis was conducted under the following conditions: 10% SDS-polyacrylamide gel, and 10 μg protein loaded per lane (protein extraction method 1). Sigma prestained molecular weight standards were run in all the gels. Gels were run in a BioRad mini-Protein II gel system. Extracellular extracts were loaded at 15–20 μl per lane, without estimating protein concentration. Voltage was kept below 200 volts during electrophoresis.

Proteins were transferred to nitrocellulose, using a Biometra semi-dry Western blot system. Nitrocellulose membranes were blocked with 5% (w/v) powdered milk for one hour, washed, incubated with anti human-PDI polyclonal antibody for between 3 hours to overnight, at dilutions ranging from 1:500 to 1:750. Membranes were washed and peroxidase-conjugated anti-rabbit IgG was added at a final dilution of 1:1000, and incubation continued for one hour. After washing the blots were developed using an Amersham ECL kit as described by the manufacturer.

Initial assays showed that strain 1072A produced secreted hPDI at levels detectable by Western blot. The level of detection was 0.05 μg of purified bovine PDI by the ECL protocol employed. This secreted PDI was shown to be a dimer since it was retained by a 100 kDa cut-off ultrafiltration membrane. When strain 1072A and its corresponding HDEL variant (1279) were compared, it was found that the human PDI was secreted by both. In this experiment the final culture/induction conditions were optimised in terms of temperature (° C.) of growth and induction period. The two strains showed a higher level of PDI synthesis when cultivated at 23° C. and then induced for 16 hours at 30° C., or when cultivated and induced at 30° C., for 16 hours.

EXAMPLE 16
Preparation of a Vector for the Expression of Antistasin in Yeast Antistasin is a potent protein inhibitor of the blood coagulation Factor Xa. Antistasin (ATS) was isolated from the salivary glands of the Mexican leech *Haementeria officinalis* (Nutt, E. et al., 1988, J. Biol. Chem., 263, pp.10162–10167). The cDNA encoding ATS was subsequently isolated and characterized by Han, J. H. et al. (1989, Gene, 75, pp.47–57). ATS is an ideal reporter protein for the evaluation of the effects of increased levels of PDI activity on the folding and formation of proper disulfide bonds in a heterologous protein secreted by recombinant yeast since ATS has 10 disulfide bonds which must be correctly paired in order for the protein to have biological activity.

ATS was expressed in yeast using the expression vector pKH4α2 (Jacobson, M. A. et al., 1989, Gene, 85, pp.511–516), which contains the galactose-inducible GAL10 promoter and the yeast MFα1 pre-pro secretory leader sequence to direct secretion of heterologous proteins.

The coding sequence for ATS was isolated by polymerase chain reaction (PCR) methods using subcloned ATS cDNA from clone λ5C-4 (Han, J. H. et al.; supra) as substrate and the oligonucleotide primers:

1. 5'-ATATGGATCCTGTCTTTGGATAAAAGA-
   CAAGGACCATTTGGACCCGGGTGT-3'   (SEQ.ID.NO.: 18)

2. 5'-TATAGGATCCTTATGATAAGCGTGGG
   ATAAGCTT-3'   (SEQ.ID.NO.: 19).

Figure 8:
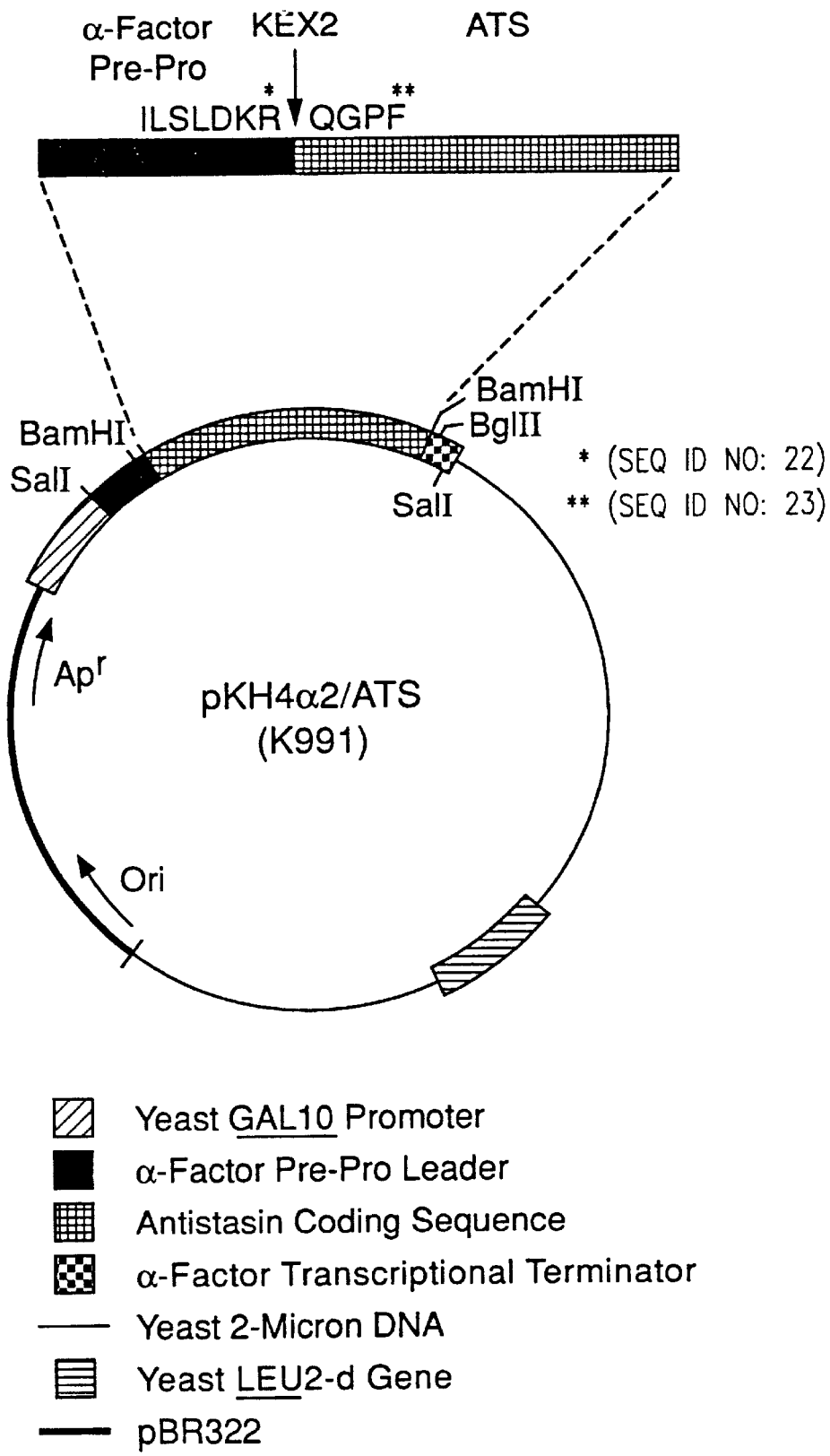
FIG. 8 illustrates the structure of plasmid pKH4α2/ATS, which is also known as K991.

Both primers contain a BamHI site to facilitate subcloning of the PCR product. The first primer inserts a yeast KEX2 yscF endoprotease cleavage site (Lys-Arg) N-terminal to the first amino acid residue of mature ATS (the yeast yscF endoprotease cleaves on the C-terminal side of the Lys-Arg site in this sequence). The PCR product was digested with BamHI, gel-purified, and then ligated into BamHI-digested pKH4α2 to yield pKH4α2/ATS (K991) (FIG. 8). This expression vector was then used to transform the yeast host strains listed in Table 1 using the spheroplast method (Hinnen, et al., 1978, supra).

Transformants were selected on synthetic solid media lacking leucine (Schultz, L. et al., 1987; Gene, 61, pp.123–133) and streaked for clonal isolates which were used in subsequent analyses. Strains were preserved by storage at −70° C. in synthetic media containing 17% glycerol.

TABLE 1

| Transformed* Strain | Host Strain | Original Strain | PDI+ Cassette |
|---|---|---|---|
| 960 | 239 | JRY188 | none |
| 1105 | 1072A | JRY188 | alpha-hPDI |
| 1176 | 1157 | JRY188 | ySP-hPDI |
| 1175 | 1148 | JRY188 | hSP-hPDI |
| 1293 | 1279 | JRY188 | alpha-hPDI(HDEL) |
| 1294 | 1267 | JRY188 | hSP-hPDI(HDEL) |
| 1295 | 1268 | JRY188 | ySP-hPDI(HDEL) |
| 1177 | 1152 | JRY188 | yPDI |
| 1156 | 548 | KHY107 | none |
| 1154 | 1136 | KHY107 | yPDI-A1 |
| 1155 | 1137 | KHY107 | yPDI-A3 |

+PDI cassettes and strains are described in the Examples as follows: alpha-hPDI, Example 9; ySP-hPDI and hSP-hPDI, Example 10; hSP-hPDI (HDEL) and ySP-hPDI (HDEL), Example 11; alpha-hPDI (HDEL) Example 12; yPDI, Example 13; yPDI-A1 and yPDI-A3, Example 14.
*Transformed strains contain the K991 antistasin expression vector.

EXAMPLE 17
Growth and Evaluation of Parental and PDI Overproducer Strains for Secretion of Antistasin The K991-transformed parental JRY188 strain plus the various transformed derivatives which overproduce either yeast or human PDI were evaluated for secretion of antistasin by the following procedure. The indicated strains were streaked from the −70° C. frozen glycerol stocks onto leucine-minus synthetic agar plates and grown for 3 days at 30° C. Culture tubes (18×150 mm) containing 5-mL of 3×YEHD [60 g Difco yeast extract, 30 g HySoy peptone, 48 g glucose per liter] media were inoculated with a small loopful of cells and incubated for about 18 hours at 23° C. on a tissue culture roller drum. At this stage, cells were induced by the addition of galactose to a final concentration of 4.8% (w/v) and the cultures were incubated for an additional 5 days at 23° C. Cells were then harvested by centrifugation and the clarified media supernatant was retained for assay of antistasin activity, which was measured by inhibition of Factor Xa activity [Nutt, E. et al., 1988, supra]. The experiment was conducted in triplicate and results are summarized in Table 2.

TABLE 2

| Strain | ng ATS per 1.0 OD | Relative Level |
|---|---|---|
| JRY188 | 25.6 | 1.0 |
| JRY188/hSP-hPDI | 24.4 | 0.95 |
| JRY188/ySP-hPDI | 28.4 | 1.11 |
| JRY188/alpha-hPDI | 77.2 | 3.0 |
| JRY188/yPDI | 65.1 | 2.54 |

EXAMPLE 18
Evaluation of Antistasin Secretion by JRY188 and Related Strains Which Overproduce HDEL Mutant Version of Human PDI The K991-transformed JRY188 and transformed derivative strains which overproduce the HDEL mutant version of human PDI with the three different secretory leaders were grown as described in Example 17 and the clarified media supernatants were evaluated for the levels of secreted ATS by the Factor Xa inhibition assay as described in Example 17. The results are presented in Table 3.

TABLE 3

| Strain | ng ATS per 1.0 OD | Relative Level |
|---|---|---|
| JRY188 | 18.0 | 1.0 |
| JRY188/hSP-hPDI(HDEL) | 27.5 | 1.53 |
| JRY188/ySP-hPDI(HDEL) | 29.3 | 1.63 |
| JRY188/alpha-hPDI(HDEL) | 31.3 | 1.74 |

EXAMPLE 19
Secretion of Antistasin by Yeast Strain KHY107 and Derivatives Which Overproduce Yeast PDI The K991-transformed KHY107 and its transformed derivatives which overproduce yeast PDI were grown up and clarified media supernatants were evaluated for the levels of secreted ATS by Factor Xa inhibition assay as described in Example 17. The results are summarized in Table 4.

TABLE 4

| Strain | ATS (mg/L) | A600 | ATS/A600 |
|---|---|---|---|
| KHY107 A1 | 0.314 | 23.9 | 0.013 |
| KHY107 A2 | 0.244 | 24.5 | 0.010 |
| KHY107 A3 | 0.334 | 25.5 | 0.013 |
| K-Y1 A1 | 1.168 | 24.8 | 0.047 |
| K-Y1 A2 | 1.469 | 21.8 | 0.067 |
| K-Y1 A3 | 1.483 | 25.3 | 0.059 |
| K-Y3 A1 | 3.856 | 39.0 | 0.099 |
| K-Y3 A2 | 2.144 | 51.2 | 0.042 |
| K-Y3 A3 | 1.920 | 48.0 | 0.040 |

K-Y1 is KHY107 with multiple copies GAL-yPDI at URA3.
KY-3 is KHY107 with single copy GAL-yPDI at URA3.
A1, A2 and A3 refer to different clonal isolates of the indicated strain evaluated in parallel.
Overexpression of yeast PDI results in 4-fold higher secretion of ATS activity on a per cell basis, and about 9-fold higher secretion on volumetric basis for isolate K-Y3-A1.

Figure 9:
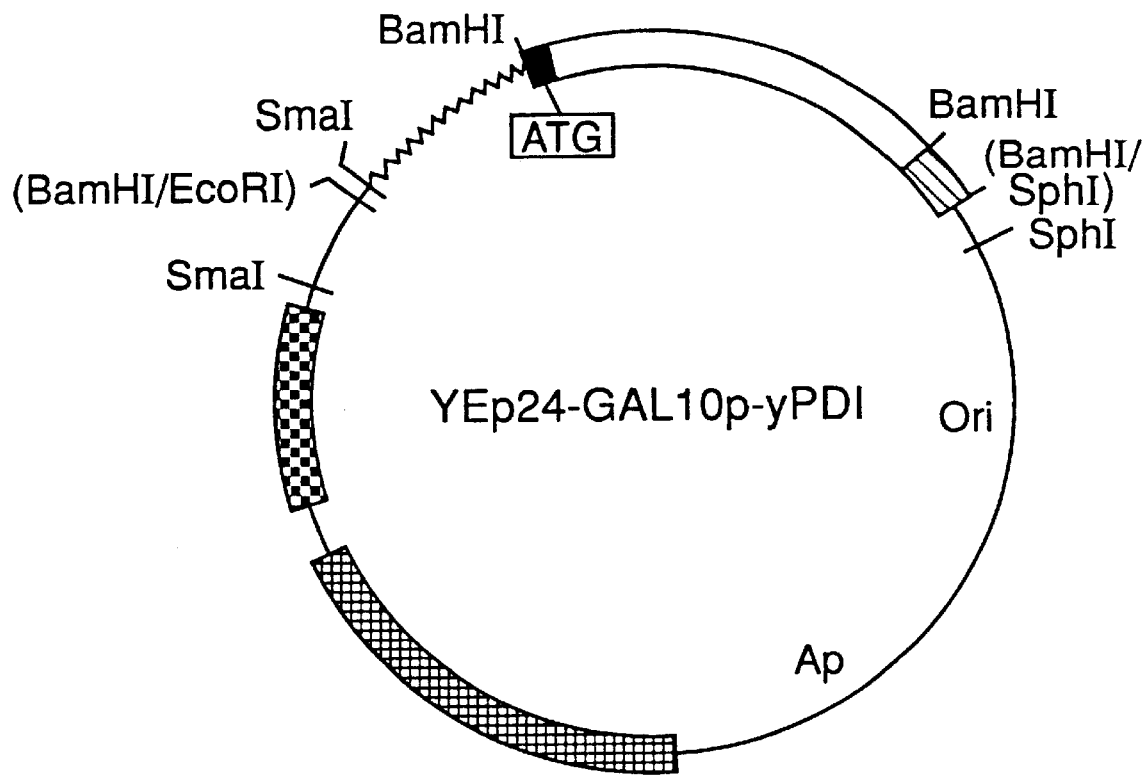
FIG. 9 illustrates the structure of YEp24-GAL10p-yPDI.
Figure 10:
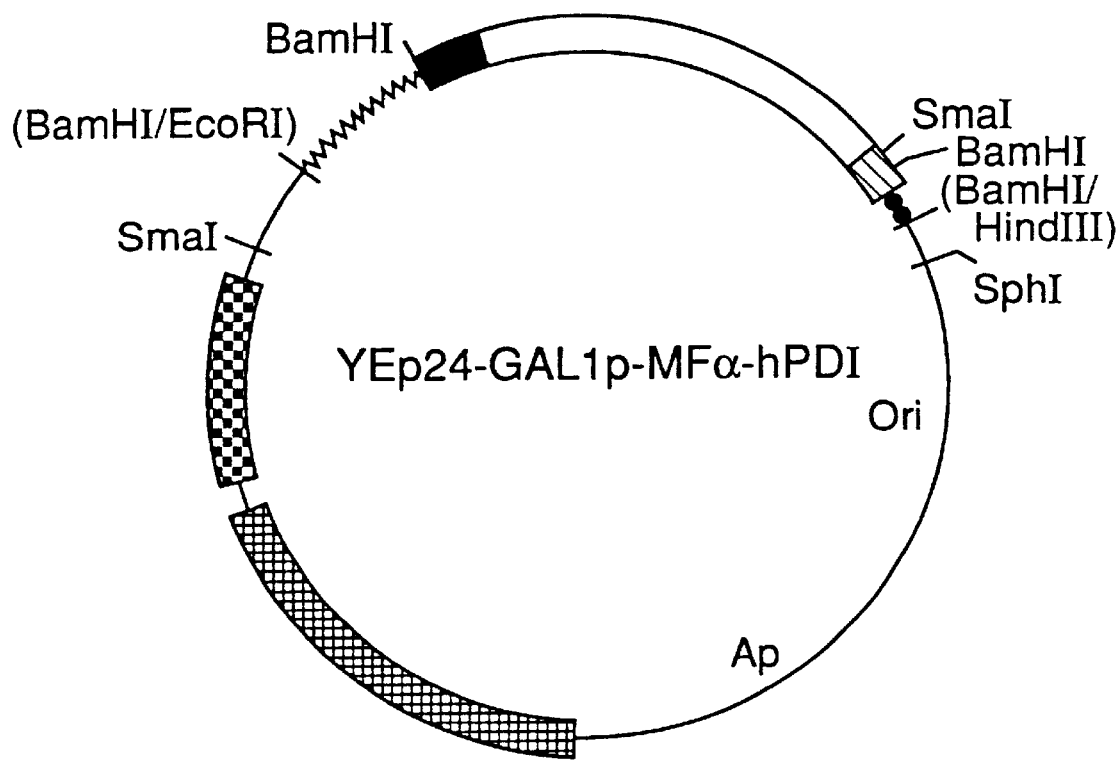
FIG. 10 illustrates the structure of YEP24-GAL1p-MFα-hPDI.

EXAMPLE 20
Construction of Yeast Host Strains Which Overproduce Either Yeast PDI or Human PDI From a Multicopy Plasmid The multicopy yeast shuttle vector YEp24 (Botstein, D. et al., 1979, Gene, 8, pp.17–24) contains the yeast 2-micron DNA origin of replication and the yeast URA3 gene for selection on uracil-minus synthetic media. YEp24 was digested with BamHI and the resulting 7.8 kbp BamHI vector fragment was gel-purified (fragment a). The plasmid pUC18-GAL10p-yPDI-ADH1t (#1015) was digested with EcoRI, SphI, and ScaI; the resulting 2.8 kbp EcoRI-SphI fragment bearing the GAL10p-yPDI-ADH1t expression cassette was gel purified (fragment b). Plasmid pUKC161 was digested with EcoRI plus HindIII and the 2.8 kbp EcoRI-HindIII fragment bearing the GAL1p—MFα1 pre-pro—human PDI expression cassette was gel purified (fragment c). The above three fragments were made flush-ended and then ligated together as follows: (1) vector fragment a and fragment b were ligated together to yield the plasmid YEp24-GAL10p-yPDI (FIG. 9); (2) vector fragment a and fragment c were ligated together to yield the plasmid YEp24-GAL1p-MFα-hPDI (FIG. 10). Large-scale CsCl preparations of the two resulting plasmid DNAs were made. In two separate transformation reactions, the yeast strain JRY188 was cotransformed with the ATS expression vector K991 (Example 16) and either YEp24-GAL10p-yPDI or YEp24-GAL1p-MFα-hPDI. Transformants containing both plasmids were selected on synthetic media lacking both leucine and uracil and isolated single colonies were restreaked on the same media for selection of clonal isolates. Five such clonal isolates for each of the two original cotransformations were inoculated into 5 ml of 3×YEHD medium in culture tubes and incubated for 24 hr at 23° C. in a tissue culture roller drum. At the end of that time, galactose was added to a final concentration of 4.8% and the cultures were incubated for an additional 5 days at 23° C. Cell were removed by centrifugation and the clarified media supernatants were assayed for the levels of ATS activity by the Factor Xa inhibition assay. The contransformants which contained the YEp24-GAL10p-yPDI plasmid plus the ATS expression vector showed 3- to 26-fold higher levels of secreted ATS activity, depending on the isolate, compared to the parental JRY188 strain containing only the ATS expression vector. The contransformants containing the YEp24-GAL1p-MFα-hPDI plasmid plus the ATS expression vector showed 2- to 3-fold higher levels of secreted ATS activity compared to the parental JRY188 strain containing only the ATS expression vector.

EXAMPLE 21

Construction and Evaluation of Yeast Host Strains Which Overproduce Either Yeast or Human PDI From the Same Expression Vector Used for Expression of a Desired Heterologous Protein The *S. cerevisiae* GAL1 and GAL10 genes are transcribed divergently from a region between the two structural genes which contains the divergent GAL1 and GAL10 promoters and a common GAL4 binding domain located between the TATA boxes for the two promoters. The plasmid pBM272 (Johnston, M. and Davis, R., 1984, Mol. Cell. Biol., 4, pp.1440) contains this divergent yeast GAL1-GAL10 promoter on a 0.85 kbp EcoRI-HindIII fragment (with also an internal BamHI site adjacent to the HindIII site). This promoter fragment was used to construct a divergent promoter cassette vector, pUC-GAL1/10, which has the following properties: yeast GAL10 promoter separated from the yeast ADH1 transcription terminator (0.35 kbp HindIII-SphI fragment) by unique EcoRI and SmaI sites, in that order. Yeast GAL1 promoter separated from a second copy of the ADH1 transcription terminator by unique BamHI and HindIII sites. The 3'-end of both ADH1 terminator elements are flanked by SphI sites to allow one to isolate the entire divergent promoter expression cassette as an SphI fragment. The vector backbone in this plasmid is pUC18 with the above expression cassette in place of the polylinker.

The plasmid pUC-GAL1/10 was digested with BamHI and gel-purified to generate fragment "a". The plasmid pUKC161 was digested with BamHI and the 1.9 kbp BamHI fragment bearing the alpha factor pre-pro leader fused in-frame to the mature human PDI coding sequence was gel-purified and ligated to vector fragment a, yielding the plasmid pUC-GAL1/10-hPDI, in which the expression of the alpha factor pre-pro—hPDI fusion is under control of the GAL1 promoter. The plasmid pUC18-GAL10p-yPDI-ADH1t (Example 13) was digested with BamHI and the resulting 1.7 Kbp BamHI fragment bearing the yeast PDI coding sequence was gel-purified and then ligated with vector fragment a, yielding the plasmid pUC-GAL1/10-yPDI in which the GAL1 promoter directs the expression of yeast PDI. These two resulting plasmids were then digested with EcoRI and made flush-ended, yielding vector fragments b and c bearing the hPDI and yPDI cassettes, respectively.

Figure 11:
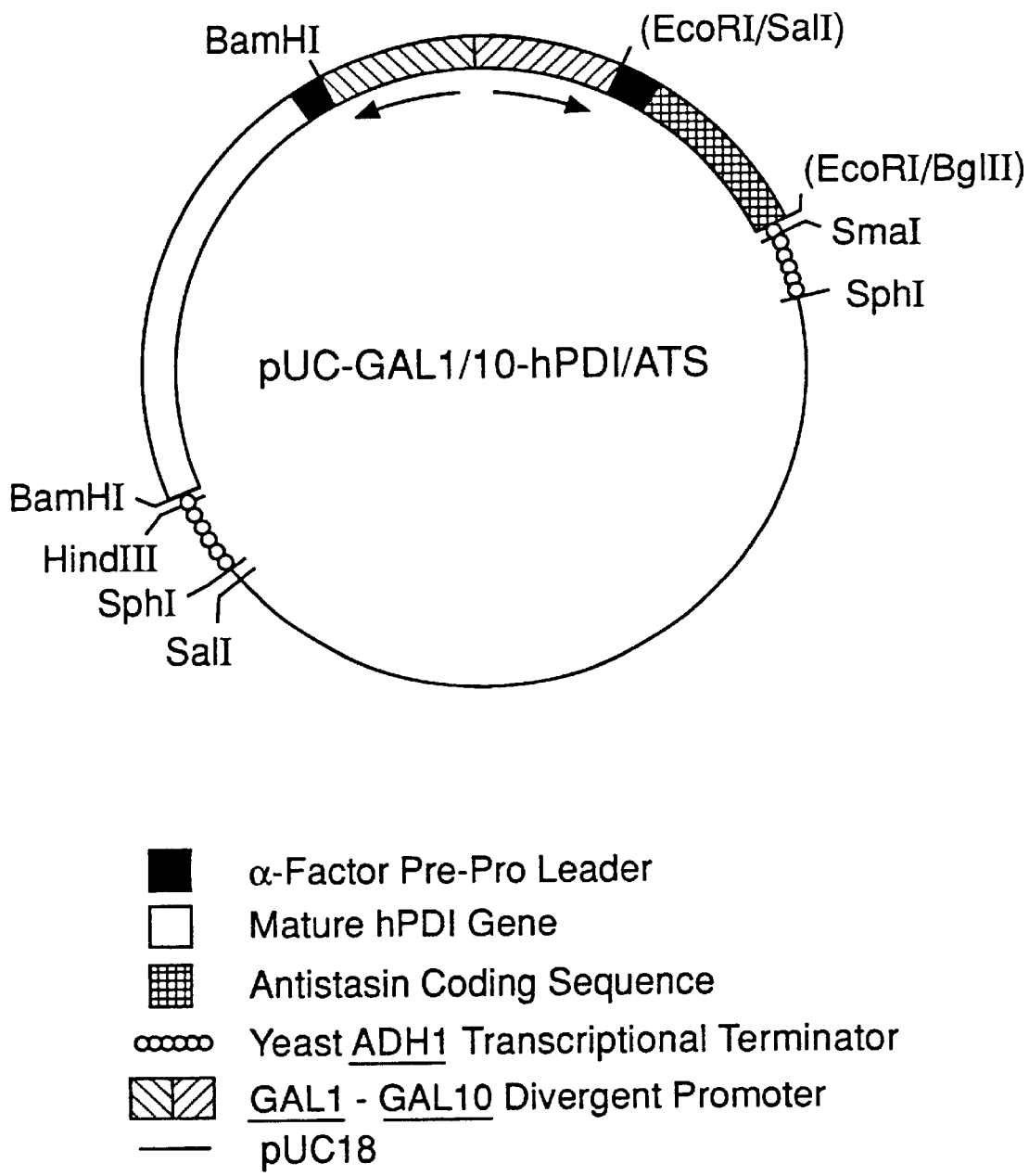
FIG. 11 illustrates the structure of pUC-GAL1/10-hPDI/ATS.
Figure 12:
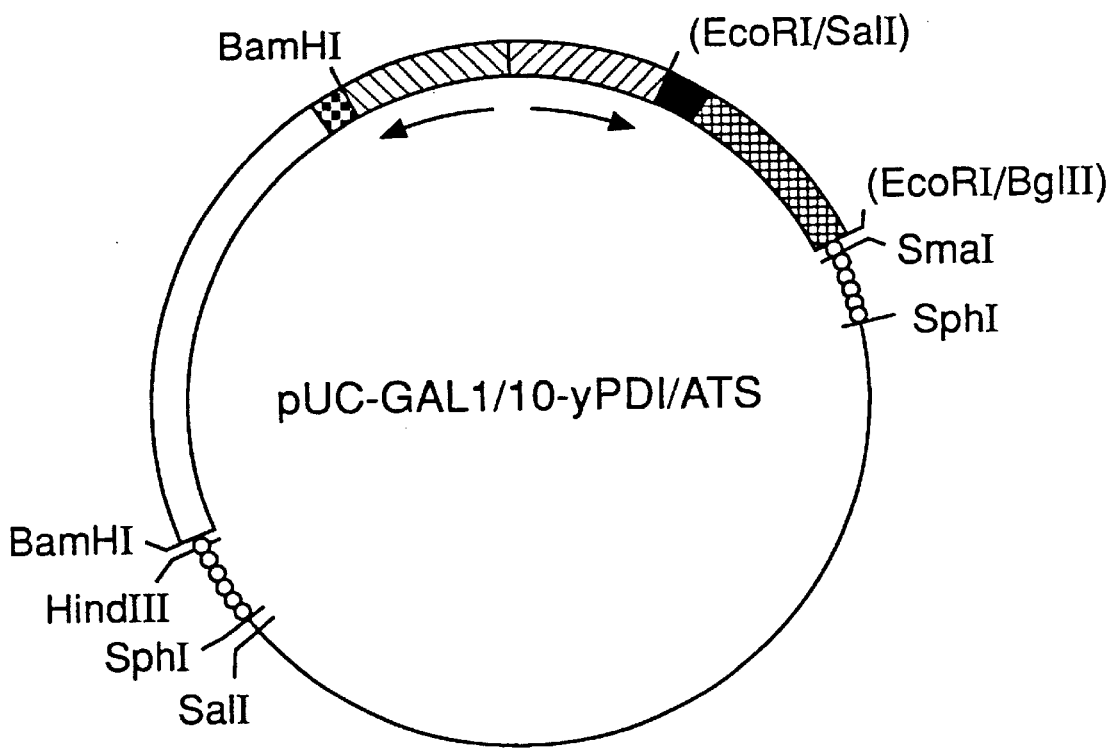
FIG. 12 illustrates the structure of pUC-GAL1/10-yPDI/ATS.

The ATS expression vector (K991) was digested with SalI plus BglII and the SalI-BglII fragment bearing the alpha factor pre-pro leader fused in-frame to the coding sequence for mature ATS was gel-purified, made flush-ended, and ligated in separate reactions to the two flush-ended vector fragments b and c. The resulting plasmids with the correct structure as determined by restriction mapping were designated pUC-GAL1/10-hPDI/ATS (FIG. 11) and pUC-GAL1/10-yPDI/ATS (FIG. 12), respectively. These two plasmids were then digested with SphI to liberate the expression cassettes and the fragments bearing either the hPDI- or yPDI-related expression cassette were ligated with the yeast shuttle vector pC1/1 (Rosenberg, S. et al. 1984, Nature, 312, pp.77–80) which had been previously digested with SphI. This yielded the resulting two plasmids, pC1/1-GAL1/10-hPDI/ATS and pC1/1-GAL1/10-yPDI/ATS, in which the ATS and PDI-related expression cassettes were present on the same high copy-number vector under control of the GAL10 and GAL1 promoters, respectively.

These two expression vectors were then used to transform yeast strains JRY188, BJ1995, and other suitable yeast host strains. Transformants were selected on leucine-minus media and the resulting transformants were evaluated for expression/secretion of ATS and PDI as described in the preceding examples.

The results presented in Table 5 (below) clearly show that the isolates which overproduce hPDI secrete several-fold higher levels of antistasin than the control strain which contained only pKH4α2/ATS. Furthermore, the isolates which overproduce yeast PDI secreted 3- to 17-fold higher levels of antistasin than the control strain.

TABLE 5

| Construct | Antistasin (mg/L)* |
|---|---|
| pC1/1-GAL1/10-hPDI/ATS | |
| Isolate 1 | 4.7 |
| Isolate 2 | 5.3 |
| Isolate 3 | 3.9 |
| Isolate 4 | 4.6 |
| Isolate 5 | 5.1 |
| pC1/1-GAL1/10-yPDI/ATS | |
| Isolate 1 | 3.9 |
| Isolate 2 | 11.7 |
| Isolate 3 | 5.8 |
| Isolate 4 | 26.0 |

TABLE 5-continued

| Construct | Antistasin (mg/L)* |
|---|---|
| Isolate 5 | 8.2 |
| JRY188 control | 1.5 |

*Yields for 5 days post-induction at 23° C.

EXAMPLE 22
Effect of Temperature on Enhanced Antistasin Secretion by PDI Overproducer Yeast Host Strains Selected isolates of strain JRY188 cotransformed with the antistasin expression vector pKH4α2/ATS and either YEp24-GAL1p-MFα-hPDI or YEp24-GAL10p-yPDI were evalutated for antistasin secretion after growth at either 23° C. or 30° C. The parent strain JRY188 transformed only with the antistasin expression vector was grown in parallel. After overnight growth in 3×YEHD medium at either 23° C. or 30° C., cell cultures were induced by the addition of galactose to a final concentration of 4.8% and propagated for an additional five days at either 23° C. or 30° C., as appropriate. Media samples harvested at 3 to 5 days post-induction were evaluated for levels of secreted antistasin by the Factor Xa inhibition assay. The results presented in Table 6 clearly show that antistasin expression was significantly higher at 23° C. than at 30° C. for all isolates overexpressing PDI, both at 3 and 5 days post-induction.

TABLE 6

| Isolate* | Temperature (° C.) | Antistasin (mg/L) 3 days | Antistasin (mg/L) 5 days |
|---|---|---|---|
| hPDI-1 | 23 | 0.83 | 2.11 |
| hPDI-2 | 23 | 1.14 | 2.68 |
| yPDI-1 | 23 | 5.93 | 10.25 |
| yPDI-3 | 23 | 3.00 | 15.92 |
| JRY188 control | 23 | 0.38 | 0.65 |
| hPDI-1 | 30 | 0.49 | 0.47 |
| hPDI-2 | 30 | 0.42 | 0.47 |
| yPDI-1 | 30 | 2.29 | 4.65 |
| yPDI-3 | 30 | 2.71 | 2.56 |
| JRY188 control | 30 | 0.34 | 0.30 |

*The various hPDI isolates contained both the antistasin expression vector K991 and YEp24-GAL1p-MFα-hPDI. The yPDI isolates contained both vector K991 and YEp24-GAL10p-yPDI.

EXAMPLE 23
Secretion of Tick Anticoagulant Peptide (TAP) by Recombinant Yeast Strains Which Overproduce PDI Tick anticoagulant peptide (TAP) is a potent, highly selective inhibitor of the blood coagulation factor Xa (Waxman, L. et al., 1990, Science, 248, pp.593–596). TAP is a novel serine protease inhibitor isolated from the tick *Ornithidoros moubata*. TAP is composed of 60 amino acids including 6 cysteine residues (Waxman et al., 1990, supra). TAP has been expressed in yeast using the expression vector pKH4-TAP which contains the galactose-inducible GAL10 promoter and the yeast MFα1 pre-pro secretory leader sequence fused in frame to the synthetic gene encoding TAP (Neeper, M. et al., 1990, J. Biol. Chem., 265, pp.17746–17752). This vector contains a slightly modified MFα1 pre-pro leader sequence due to the presence of a BamHI cloning site located at the position of amino acid 79 of the pre-pro leader (Neeper et al, 1990, supra).

A second TAP expression vector, pKH4-3B/TAP, was constructed which contains the authentic MFα1 pre-pro leader sequence fused in-frame to the synthetic gene encoding TAP. The plasmid pKH4-TAP containing the synthetic TAP gene (Neeper et al., 1990, supra) was used as the DNA template in a polymerase chain reaction (PCR) using the following two oligonucleotide primers in order to modify the 5'- and 3'- termini of the synthetic TAP gene, respectively:

5'-TACAACCGTC TGTGCATCAA-'3   (SEQ.ID.NO.:20)

and

5'-ACTGGATCCG AATTCAAGCT TAG
   ATGCAAG CGT-3'   (SEQ.ID.NO.:21).

The PCR reaction was carried out by methods well known to those of ordinary skill in the art (Innis, M. A. et al., editors, 1990, PCR Protocols: A Guide to Methods and Applications, Academic Press, Inc., San Diego Calif.). The resulting PCR product was phosphorylated with T4 polynucleotide kinase, digested with BamHI, and then gel-purified to yield a 0.2 kbp blunt-BamHI fragment containing the blunt end at the exact 5'-end of the TAP coding sequence and a cohesive BamHI end on the 3'-side of the translation termination codon.

The vector pKH4-3B (Hofmann, K. and Schultz, L. D., 1991, Gene, 101, pp.105–111) contains a unique SphI site at the 3'-end of the MFα1 pre-pro leader coding sequence. pKH4-3B was digested with SphI, made flush-ended by treatment with T4 DNA polymerase, and then digested with BglII. The resulting blunt-BglII vector fragment was gel-purified and ligated with the aforementioned 0.2 kbp blunt-BamHI TAP fragment to yield the vector pKH4-3B/TAP.

In separate transformation reactions, the yeast strains BJ1995, JRY188, and U9 were cotransformed with the vectors YEp24-GAL10p-yPDI plus either pKH4-TAP or pKH4-3B/TAP. Cotransformants containing both plasmids were selected on synthetic medium lacking both leucine and uracil and isolated single colonies were restreaked on the same medium for selection of clonal isolates. Three such clonal isolates for each of the different vector/host cotransformations were inoculated into 5-mL of modified 5×Leu⁻ media lacking uracil (5×Leu⁻Ura⁻) and containing 4% glucose in culture tubes. The cultures were incubated for 24 hours at 30° C. in a tissue culture roller drum. At the end of that time, the cells were recovered by centrifugation and resuspended in 5 mL of 5×Leu⁻Ura⁻ medium containing 4% galactose. The resulting cultures were incubated at 30° C. for an additional 48 hours. Cells are then removed by centrifugation and clarified media samples evaluated for the levels of secreted TAP by SCX-HPLC or Factor Xa inhibition assay (Waxman et al., 1990, supra). As an alternative approach, the recombinant yeast cells are grown for 24 hours at 23° C., induced by addition of galactose to 4% final concentration, and then incubated for an additional five days at 23° C. Clarified media samples are then evalutated for the levels of secreted TAP as described above.

What is claimed is:

1. An in vivo process for producing disulfide-bonded recombinant proteins which comprises overexpressing recombinant protein disulfide isomerase from one or more recombinant expression cassettes containing a gene encoding protein disulfide isomerase and overexpressing one or more recombinant genes encoding one or more disulfide-bonded proteins other than protein disulfide isomerase from a recombinant expression cassette within a recombinant host cell, wherein production of properly folded disulfide-bonded protein is greater than the amount of properly folded disulfide-bonded protein produced in the absence of protein disulfide isomerase overexpression.

2. The process according to claim 1, wherein the expression cassettes encoding protein disulfide isomerase are integrated into the host cell genome.

3. The process according to claim 1, wherein the expression cassettes encoding protein disulfide isomerase are contained on autonomously replicating plasmids.

4. The process according to claim 1 wherein the recombinant protein disulfide isomerase gene is contained within one or more expression cassettes contained on one or more plasmids, and the recombinant genes encoding one or more disulfide bonded proteins are contained on one or more plasmids.

5. The process according to claim 1 wherein the recombinant protein disulfide isomerase gene is contained within one or more expression cassettes contained on one or more plasmids, and the recombinant genes encoding one or more disulfide bonded proteins are integrated into the host cell genome.

6. The process according to claim 1 wherein the recombinant genes encoding one or more disulfide bonded proteins are integrated into the host cell genome.

7. The process according to claim 1 wherein the recombinant expression cassettes encoding the protein disulfide isomerase and the recombinant genes are contained on the same plasmid.

8. The process according to claim 1 wherein the recombinant host cell is mammalian.

9. The process according to claim 1 wherein the recombinant host cell is yeast.

10. The process according to claim 1 wherein the recombinant gene is antistasin.

11. The process according to claim 1 wherein the recombinant gene is tick anticoagulant protein.

12. The process according to claim 1 wherein the protein disulfide isomerase gene is a yeast protein disulfide isomerase gene.

13. The process according to claim 1 wherein the protein disulfide isomerase gene is a mammalian protein disulfide isomerase gene.

14. The process according to claim 9 wherein the protein disulfide isomerase gene is a yeast protein disulfide isomerase gene.

15. The process according to claim 9 wherein the yeast is a strain of species of the families Saccharomycetaceae or Cryptococcaceae.

16. The process according to claim 13 wherein the protein disulfide isomerase gene is a human protein disulfide isomerase gene.

17. The process according to claim 15 wherein the yeast is a species of the genus Saccharomyces.

18. The process according to claim 15 wherein the protein disulfide isomerase gene is a yeast protein disulfide isomerase gene.

19. The process according to claim 17 wherein the yeast is *Saccharomyces cerevisiae*.

20. The process according to claim 17 wherein the protein disulfide isomerase gene is a yeast protein disulfide isomerase gene.

21. The process according to claim 19 wherein the protein disulfide isomerase gene is a yeast protein disulfide isomerase gene.

22. An in vivo process for producing a disulfide bonded secreted recombinant proteins which comprises overexpressing recombinant protein disulfide isomerase from a recombinant expression cassette containing a gene encoding protein disulfide isomerase and overexpressing one or more recombinant genes encoding one or more disulfide-bonded proteins other than protein disulfide isomerase from a recombinant expression cassette within a recombinant yeast host cell, wherein the disulfide bonded recombinant protein is secreted into and recovered from the media and wherein the amount of properly folded disulfide-bonded protein is greater than the amount of properly folded disulfide-bonded protein produced in the absence of protein disulfide isomerase overexpression.

23. The process according to claim 22 wherein the protein disulfide isomerase gene is a yeast protein disulfide isomerase gene.

24. The process according to claim 22 wherein the protein disulfide isomerase gene is a mammalian protein disulfide isomerase gene.

25. The process according to claim 22, wherein the recombinant yeast host cell overexpressing protein disulfide isomerase contains one or more copies of a recombinant expression cassette encoding protein disulfide isomerase.

26. The process according to claim 22 wherein the protein disulfide isomerase gene is contained within one or more expression cassettes contained on one or more plasmids, and the recombinant genes encoding the disulfide-bonded proteins are contained on one or more plasmids.

27. The process according to claim 22 wherein the recombinant yeast host cell is grown at a temperature less than 30° C. for expression of one or more disulfide bonded proteins.

28. The process according to claim 22 wherein the recombinant yeast host cell is a strain of the genus Saccharomyces.

29. The process according to claim 28 wherein the recombinant yeast host cell is a strain of the species *Saccharomyces cerevisiae*.

30. The process according to claim 23 wherein the recombinant yeast host cell is a strain of the genus Saccharomyces.

31. The process according to claim 24 wherein the protein disulfide isomerase gene is a human protein disulfide isomerase gene.

32. The process according to claim 25 wherein the recombinant expression cassettes encoding protein disulfide isomerase are integrated into the yeast host cell genome.

33. The process according to claim 25 wherein the recombinant expression cassettes encoding protein disulfide isomerase are contained on autonomously replicating plasmids.

34. The process according to claim 26 wherein the expression cassette encoding the protein disulfide isomerase and the recombinant genes are contained on the same plasmid.

35. The process according to claim 27 wherein the recombinant yeast host cell is grown at a temperature between approximately 20° C. to 26° C. for expression of one or more disulfide-bonded proteins.

36. The process according to claim 30 wherein the recombinant yeast host cell is a strain of the species *Saccharomyces cerevisiae*.

37. The process according to claim 35 wherein the disulfide-bonded protein is antistasin.

38. The process according to claim 35 wherein the disulfide-bonded protein is tick anticoagulant protein.

39. A strain of the yeast *Saccharomyces cerevisiae* which overexpresses recombinant protein disulfide isomerase from a recombinant expression cassette containing a gene encoding protein disulfide isomerase and overexpressing one or more recombinant genes encoding one or more disulfide bonded proteins other that protein disulfide isomerase from a recombinant expression cassette.

40. The strain of yeast according to claim 39 wherein the protein disulfide isomerase is human protein disulfide isomerase.

41. The strain of yeast according to claim 39 wherein the protein disulfide isomerase is yeast protein disulfide isomerase.

* * * * *